United States Patent
Brandt

(10) Patent No.: US 11,919,939 B2
(45) Date of Patent: Mar. 5, 2024

(54) BETA-2-GLYCOPROTEIN 1 DERIVED PEPTIDE AND USE THEREOF FOR TREATING ANTIPHOSPHOLIPID SYNDROME

(71) Applicant: Université de Genéve, Geneva (CH)

(72) Inventor: Karim Brandt, Geneva (CH)

(73) Assignee: Université de Genève, Geneva (CH)

( * ) Notice: Subject to any disclaimer, the term of this patent is extended or adjusted under 35 U.S.C. 154(b) by 388 days.

(21) Appl. No.: 16/615,460

(22) PCT Filed: May 23, 2018

(86) PCT No.: PCT/EP2018/063439
§ 371 (c)(1),
(2) Date: Nov. 21, 2019

(87) PCT Pub. No.: WO2018/215506
PCT Pub. Date: Nov. 29, 2018

(65) Prior Publication Data
US 2020/0172596 A1    Jun. 4, 2020

(30) Foreign Application Priority Data
May 23, 2017    (EP) .................................... 17172584

(51) Int. Cl.
| C07K 14/74 | (2006.01) |
| C07K 7/06 | (2006.01) |
| G01N 33/564 | (2006.01) |
| A61K 38/00 | (2006.01) |

(52) U.S. Cl.
CPC .......... *C07K 14/70539* (2013.01); *C07K 7/06* (2013.01); *G01N 33/564* (2013.01); *A61K 38/00* (2013.01); *G01N 2800/24* (2013.01)

(58) Field of Classification Search
CPC ............ A61K 2300/00; A61K 47/6811; A61K 38/00; A61K 51/088; A61K 49/14; C07K 2317/24; C07K 2317/73; C07K 2319/00; C07K 7/06; C07K 14/70539; C07K 2317/33; G01N 33/564; G01N 33/92; G01N 2800/24; G01N 2405/04
See application file for complete search history.

(56) References Cited

U.S. PATENT DOCUMENTS

| 2005/0107585 A1* | 5/2005 | Murray .................... C12N 9/88 530/350 |
| 2009/0068207 A1* | 3/2009 | Breitbart .................... A61P 9/00 424/184.1 |
| 2014/0221282 A1* | 8/2014 | Sun ........................ A61K 47/60 530/308 |
| 2015/0064169 A1* | 3/2015 | Wang ..................... C07K 16/38 424/130.1 |

FOREIGN PATENT DOCUMENTS

| GB | WO2017025610 A1 * | 2/2017 | ........... C07K 14/705 |
| IL | WO2006109312 A2 * | 10/2006 | ............. A61K 38/17 |
| WO | WO-2006109312 A2 | 10/2006 | |
| WO | WO-2010075604 A1 | 7/2010 | |

OTHER PUBLICATIONS

STN CAS Registry: Exact and pattern searching of protein sequences. Nov. 2008. (Year: 2008).*
Wang et al. Epitope specificity of monoclonal anti-beta 2-glycoprotein I antibodies derived from patients with the antiphospholipid syndrome. J Immunol 1995; 155:1629-1636. (Year: 1995).*
Beer et al. Immobilized Arg-Gly-Asp (RGD) Peptides of Varying Lengths as Structural Probes of the Platelet Glycoprotein IIb/IIIa Receptor. Blood, vol. 79, No. 1 Jan. 1, 1992: pp. 117-128. (Year: 1992).*
Bacart et al. The BRET technology and its application to screening assays. Biotechnol. J. 2008; 3: 311-324. (Year: 2008).*
Vlachoyiannopoulos, P. G., et al., "Anti-CD40 antibodies in antiphospholipid syndrome and systemic lupus erythematosus," Thromb Haemost, (92): 1303-1311 (2004).
Bas De Laat and Philip G. de Groot, "Autoantibodies Directed Against Domain I of Beta2-Glycoprotein I," Current Rheumatology Reports, 13(1): 70-76 (2011).
Kuwana, M., "$\beta_2$-glycoprotein I: antiphospholipid syndrome and T-cell reactivity," Thrombosis Research, 114(5-6): 347-355 (2004).
Blank, M., et al., "Prevention of experimental antiphospholipid syndrome and endothelial cell activation by synthetic peptides," Proceedings of the National Academy of Science US, 96(9): 5164-5168 (1999).
Moerloose, P. D., et al., "Patient-derived anti-$\beta$2GP1 antibodies recognize a peptide motif pattern and not a specific sequence of residues," Haematologica, 102(8): 1324-1332 (2017).
International Search Report from PCT Application No. PCT/EP2018/063439 dated Jun. 28, 2018.
Written Opinion from PCT Application No. PCT/EP2018/063439 dated Jun. 28, 2018.

* cited by examiner

*Primary Examiner* — Aradhana Sasan
*Assistant Examiner* — Jia-Hai Lee
(74) *Attorney, Agent, or Firm* — Harness Dickey & Pierce P.L.C.

(57) ABSTRACT

The invention provides an isolated peptide containing a motif that binds antiphospholipid antibodies (aPLA) and that is recognized by CD4+ T cells that are able to induce production of antiphospholipid antibodies (aPLA). The present invention further provides methods for detection of aPLA and CD4+ T cells able to induce production of aPLA. The present invention also provides methods for treating the antiphospholipid syndrome (APS).

19 Claims, 8 Drawing Sheets
Specification includes a Sequence Listing.

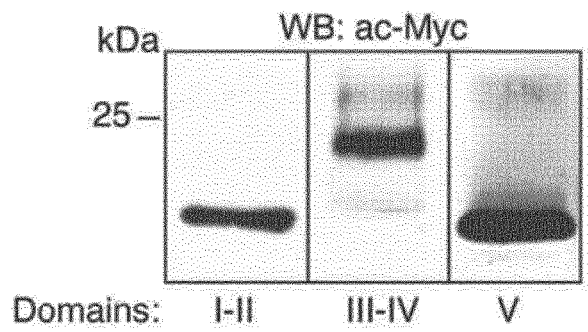
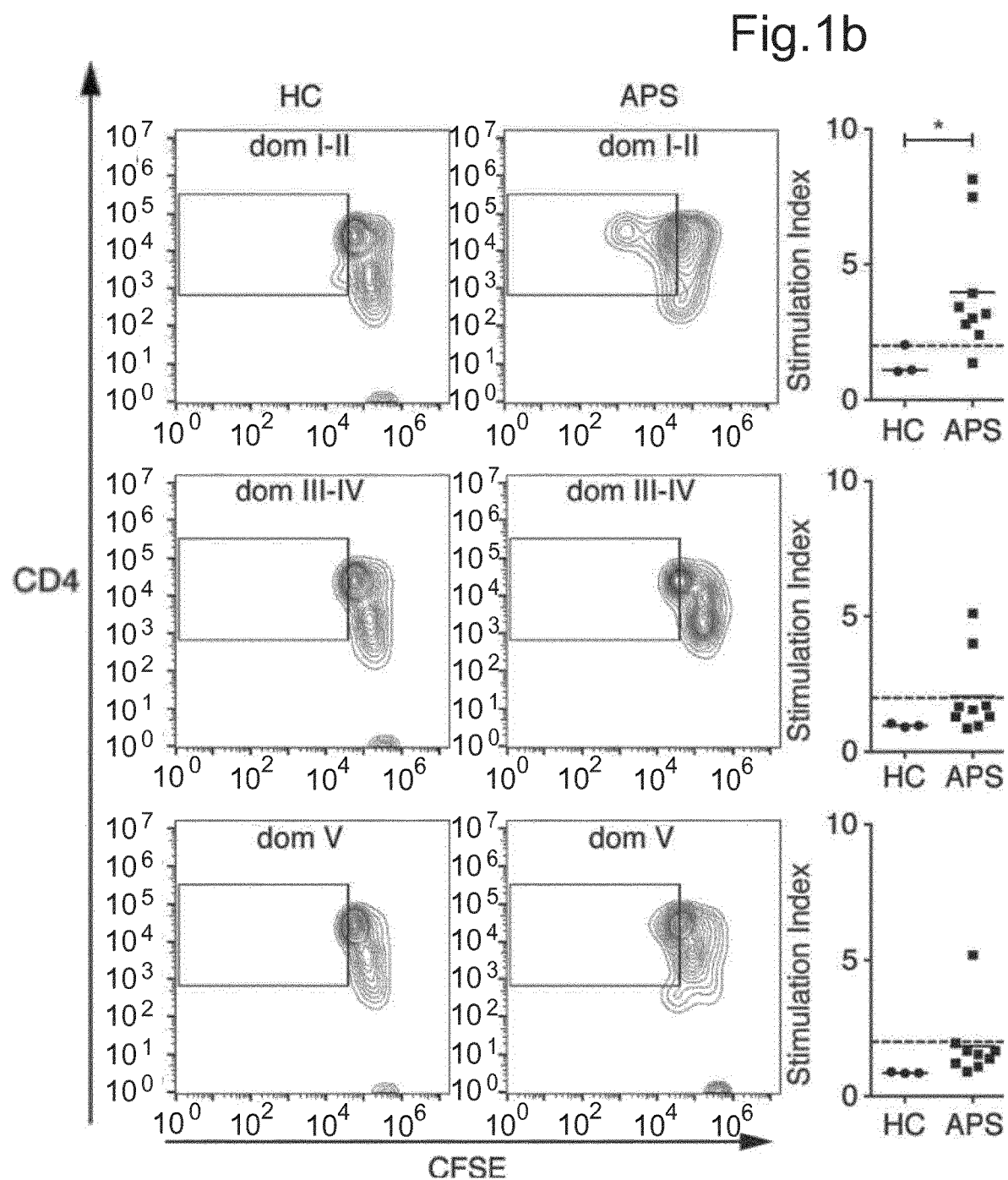

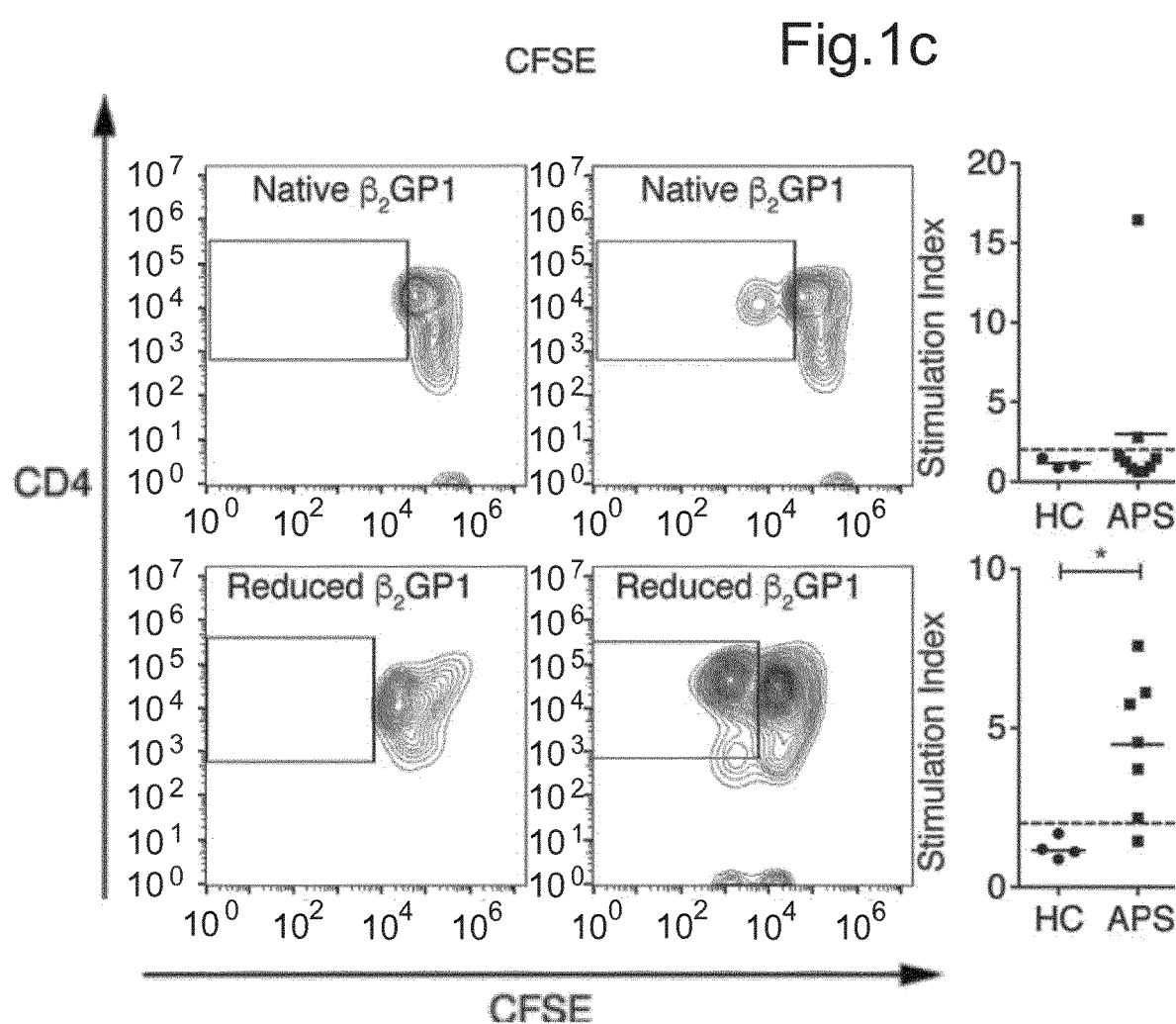

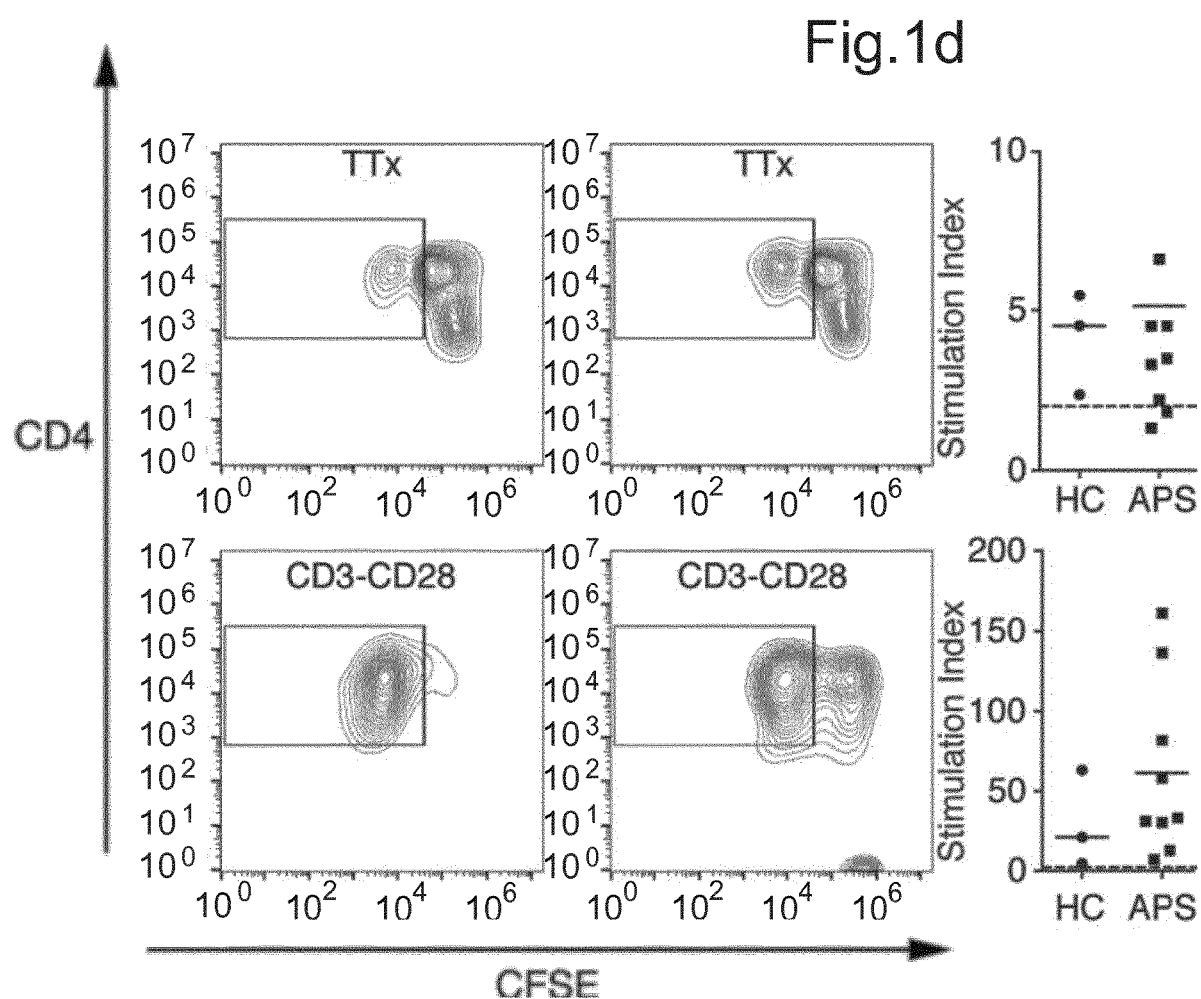

Fig.2a
| Pooled-peptides of Domain I-II | Peptides | Water soluble |
|---|---|---|
| Pool I | 2; 3; 5; 7 | Yes |
| Pool II | 8; 9; 12; 13 | Yes |
| Pool III | 1; 4; 6; 10; 11 | No |
Fig.2b
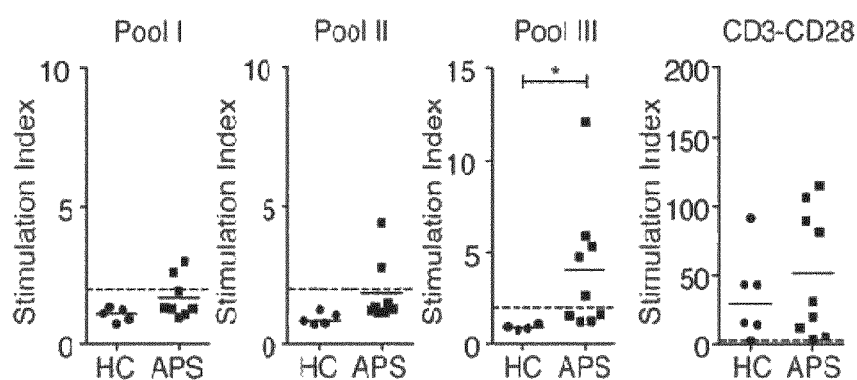
Fig.2c
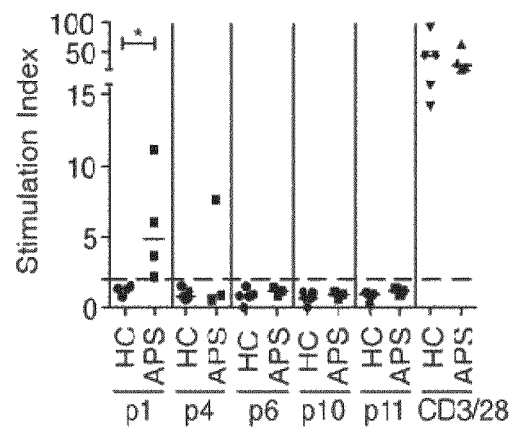

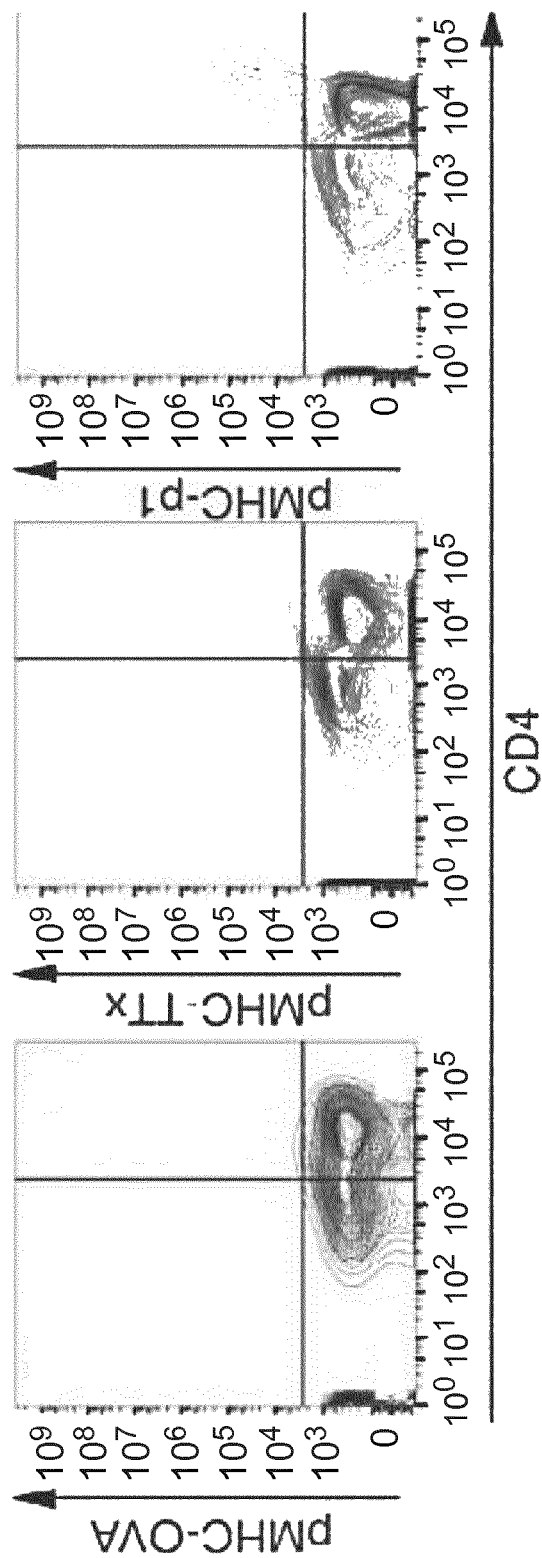

BETA-2-GLYCOPROTEIN 1 DERIVED PEPTIDE AND USE THEREOF FOR TREATING ANTIPHOSPHOLIPID SYNDROME

FIELD OF THE INVENTION

The invention provides an isolated peptide containing a motif that binds antiphospholipid antibodies (aPLA) and that is recognized by CD4+ T cells that are able to induce production of antiphospholipid antibodies (aPLA). The present invention further provides methods for detection of aPLA and CD4+ T cells able to induce production of aPLA. The present invention also provides methods for treating the antiphospholipid syndrome (APS).

BACKGROUND OF THE INVENTION

The antiphospholipid syndrome (APS) is described as a common risk factor for recurrent thromboembolic events and/or pregnancy complications resulting from circulating antiphospholipid antibodies (aPLA).[1] It is now widely accepted that the plasma phospholipid binding protein β-2-Glycoprotein 1 (β2GP1) is the main antigenic target for aPLA.[2] β2GP1 is a protein of 43 kDa composed of 5 short consensus repeat domains called "sushi" domains. Two different conformations exist for β2GP1: a circular plasma conformation and a fishhook conformation.[3] Epitopes within domains I and V are involved in maintaining a circular conformation, whereas binding of domain V to anionic surfaces induces a fishhook conformation and exposure of a cryptic epitope in domain I.[3, 4] This cryptic epitope is described as being located around residues 39 and 43; however, Iverson et al. have identified additional residues involved in the recognition by pathogenic anti-β2GP1 antibodies in domain I.[5, 6] Ioannou et al. have also studied mutations including residues R39 to R43 describing complex and probably discontinuous epitopes.[7] Their data suggest that the epitope(s) are not "classical" or that several epitopes are present in domain I and could potentially even be present elsewhere in β2GP1.

Humoral immunophysiology studies of APS and the treatment of APS patients with an anti-CD20 monoclonal antibody (rituximab) have aroused interest in B cells as therapeutic targets. Anti-CD20-treated APS patients have a normal distribution of anti-β2GP1, anti-cardiolipin (aCL) and Lupus anticoagulant (LAC) antibody titers and improved clinical manifestations.[8] The isotype of anti-β2GP1 antibody is mainly IgG, suggesting that the production of these antibodies requires antigen-specific CD4+ T helper cells.[9] Hattori et al. have shown that β2GP1 induce an in vitro proliferative response of T cells from APS patients. These β2GP1-specific CD4+ T cells are able to induce the production of anti-β2GP1 antibodies by autologous peripheral blood B cells through HLA-DR interactions.[10, 11] The identity of the principal T cell epitopes on β2GP1 has not been established yet. It seems that all five β2GP1 domains are able to induce a T cell proliferative response depending on APS patients.[11] Moreover, analysis of T cell responses to a β2GP1-derived peptide library have shown that CD4+ T cells are reactive to different peptides independently of HLA.[12] It was previously demonstrated that β2GP1-specific T cells are present in APS patients although the specific domain(s) and peptide(s) inducing T cell proliferation were not well defined.[11, 12] Therefore, there is still a need to identify β2GP1-domain-specific T cells in APS patients. In addition, even though different tools are used, the diagnosis of APS patients currently is laborious and time-consuming. Hence, there is a need for a diagnostic tool and method that allows for improved diagnosis of APS, in particular with high sensitivity and high specificity.

SUMMARY OF THE INVENTION

Thus an aspect of the present invention provides an isolated peptide having the amino acid sequence SEQ ID NO:51

$$X_1\text{-}X_2\text{-}X_3\text{-}X_4\text{-}X_5\text{-}F\text{-}X_7\text{-}X_8$$

wherein
  X1, X2, X3 and X8 are nonpolar amino acid residues, each independently selected from the group comprising A, V, I, L, M, F, W, C, P and G,
  X4 and X5 are polar amino acid residues, each independently selected from the group comprising Y, T, S, H, K, R, E, D, Q and N,
  X7 is any amino acid residue selected from the group comprising A, V, I, L, M, F, W, C, P, G, Y, T, S, H, K, R, E, D, Q and N.

Another aspect of the present invention provides a MHC composition comprising MHC class II molecules and the peptide of the invention.

Another aspect of the present invention provides a pharmaceutical composition comprising the peptide of the invention in an amount effective to prevent, reduce or inhibit one or more symptoms of the antiphospholipid syndrome (APS) in a subject in need thereof, and a pharmaceutically acceptable carrier for administration of the peptide.

Another aspect of the present invention provides a method for treating the antiphospholipid syndrome (APS) in a subject comprising administering to said subject a therapeutically effective amount of the MHC composition of the invention.

Another aspect of the present invention provides the MHC composition of the invention for use in treatment of the antiphospholipid syndrome (APS).

Another aspect of the present invention provides a method for preventing and/or inhibiting one or more symptoms of the antiphospholipid syndrome (APS) in a subject comprising administering to said subject a therapeutically effect amount of the peptide of the invention or the pharmaceutical composition of the invention.

Another aspect of the present invention provides the peptide of the invention for use in a method for preventing and/or inhibiting one or more symptoms of the antiphospholipid syndrome (APS).

Another aspect of the present invention provides a method for diagnosing of an antiphospholipid syndrome (APS) in a subject, wherein presence or absence of an antiphospholipid antibody (aPLA) is detected in a sample from the subject diagnosed, and wherein the presence of an antiphospholipid antibody is indicative of the APS disease and wherein the antiphospholipid antibody is detected using an immunoassay comprising the steps of
  (i) providing a sample;
  (ii) contacting the sample with the peptide of the invention under conditions allowing for the formation of a complex between antiphospholipid antibodies with the peptide of the invention;
  (iii) detecting the complex.

Another aspect of the present invention provides a method for detecting the presence of antiphospholipid antibody in a sample comprising
(i) providing a sample,
(i) contacting the sample with the peptide of the invention under conditions allowing for the formation of a complex between antiphospholipid antibodies with the peptide of the invention;
(iii) detecting the complex using an immunoassay.

Another aspect of the present invention provides use of the peptide of the invention for detecting antiphospholipid antibodies.

Another aspect of the present invention provides a method for diagnosing of an antiphospholipid syndrome (APS) in a subject, wherein presence or absence of CD4+ T cells, able to induce production of antiphospholipid antibodies, is detected in a sample from the subject diagnosed, and wherein the presence of said CD4+ T cells is indicative of the APS disease, comprising the steps of
(i) providing a sample;
(ii) contacting the sample with the MHC composition of the invention;
(iii) detecting CD4+ T cells by measuring the binding of said composition with CD4+ T cells in said sample, wherein the binding of the composition to a CD4+ T cell is indicative for the presence of CD4+ T cells in said sample.

Another aspect of the present invention provides use of the MHC composition of the invention for the detection, preparation or depletion of CD4+ T cells.

Another aspect of the present invention provides a kit for detecting in a sample the presence or absence of an antiphospholipid antibody, the kit comprising the peptide of the invention.

Another aspect of the present invention provides a kit for detecting in a sample the presence or absence of CD4+ T cells able to induce production of antiphospholipid antibodies, the kit comprising the MHC composition of the invention.

BRIEF DESCRIPTION OF THE FIGURES

FIG. 1 shows domain I-II and reduced β2GP1 induce proliferation of T cells from APS patients. (A) β2GP1 recombinant domains are purified and analyzed by Western blot. Data are representative of three independent experiments. (B-D) Flow cytometry analysis of the proliferation assay performed on PBMC of APS patients in the presence of domains I-II, II-IV, V β2GP1, reduced β2GP1 and tetanus toxin (TTx). CD3-CD28 is positive proliferation control. CD4$^+$CFSE$^{low}$ population is gated on CD3$^+$ cells. Data are mean±SEM of 9 different donors. Statistical significance was determined by Mann-Whitney U analysis.

FIG. 2 shows peptide 1 of β2GP1 carries antigenic determinant for CD4$^+$ T cell proliferation. (A) Table of peptide distribution for proliferation assay. (B) Flow cytometry analysis of proliferation assay performed on PBMC of APS patients in the presence of pool I, II or III. CD3-CD28 shows positive proliferation control. (C) Flow cytometry analysis of proliferation assay performed on the PBMC of APS patients in the presence of p1 (SEQ ID NO:32), p4 (SEQ ID NO:35), p6 (SEQ ID NO:33), p10 (SEQ ID NO:44) and p11 (SEQ ID NO:45). CD3-CD28 is positive proliferation control. CD4$^+$CFSE$^{low}$ population is gated on CD3$^+$ cells. Data are mean±SEM of 9 different donors. Statistical significance was determined by Mann-Whitney U analysis. (D) Flow cytometry analysis of pMHC class II tetramer staining loaded with p1 (SEQ ID NO:32) on PBMS of APS patients pulsed with recombinant domain I-II. pMHC-OVA (ovalbumin), pMHC-TTx (Tetanus toxin) are negative controls. Populations are gated on CD3$^+$ cells.

DETAILED DESCRIPTION OF THE INVENTION

Figure 3A:
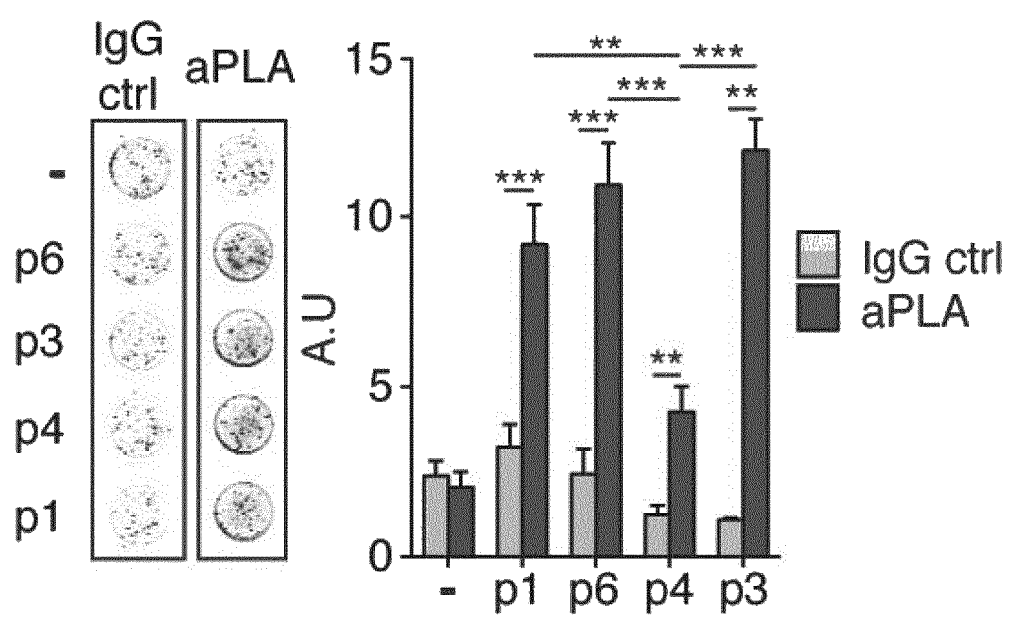
FIG. 3 shows aPLA epitope contains $X_1$-$X_2$-$X_3$-$X_4$-$X_5$-F-$X_7$-$X_8$ motifs. Representative picture of IgG ctl (control) or aPLA binding to peptides-coated well. Quantification of aPLA binding to p1- (SEQ ID NO:32), p6- (SEQ ID NO:33), p4- (SEQ ID NO:35) and p3- (SEQ ID NO:39) coated wells. Data are mean±SEM of 9 different donors. Statistical significance was determined by Mann-Whitney U analysis.

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components. Also as used in the specification and claims, the language "comprising" can include analogous embodiments described in terms of "consisting of" and/or "consisting essentially of".

As used in the specification and claims, the singular forms "a", "an" and "the" include plural references unless the context clearly dictates otherwise.

As used in the specification and claims, the term "and/or" used in a phrase such as "A and/or B" herein is intended to include "A and B", "A or B", "A", and "B".

As used herein, an "amino acid molecule" or "amino acid residue" refers to any naturally occurring amino acid, any amino acid derivative or any amino acid mimic known in the art, including modified or unusual amino acids. In certain embodiments, the residues of the peptide are sequential, without any non-amino acid interrupting the sequence of amino acid residues. In other embodiments, the sequence may comprise one or more non-amino acid moieties, for example linkers.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder, such as the antiphospholipid syndrome (APS). In other embodiments, the subject is a subject in need to prevent and/or inhibit symptoms of the antiphospholipid syndrome (APS). The term does not denote a particular age or sex. Thus, adult and newborn subjects, whether male or female, are intended to be covered.

The present invention is based on the surprising finding that the binding peptide epitope for antiphospholipid antibodies (aPLA) and CD4+ T cell is determined by the polarity of amino acids and not by the amino acid sequence. Indeed, a sequence in the domain I of β2GP1 that triggers a CD4+ T cell proliferation has been characterized. A comparison of this sequence with the previously reported aPLA-binding discontinuous epitope R39-R43 reveals the presence of an indeterminate motif in β2GP1 in which the polarity determines the characteristics and specificity of aPLA-interacting motifs. It has been further demonstrated in vitro that peptides and domains of β2GP1 containing these motifs were able to interact with aPLA and to inhibit their monocyte activating activity. Such finding provides surprisingly for both high sensitivity and high specificity diagnostic tools and treatment methods.

An aspect of the invention provides an isolated peptide having the amino acid sequence SEQ ID NO: 51

$X_1$-$X_2$-$X_3$-$X_4$-$X_5$-F-$X_7$-$X_8$ wherein

- X1, X2, X3 and X8 are nonpolar amino acid residues, each independently selected from the group comprising A, V, I, L, M, F, W, C, P and G. In some preferred embodiments, X8 is C amino acid residue,
- X4 and X5 are polar amino acid residues, each independently selected from the group comprising Y, T, S, H, K, R, E, D, Q and N,
- X7 is any amino acid residue, preferably any natural L-amino acid residue, more preferably X7 is any amino acid residue selected from the group comprising A, V, I, L, M, F, W, C, P, G, Y, T, S, H, K, R, E, D, Q and N.

The isolated peptide of the invention can have the reversed amino acid sequence (reading from C- to N-terminus), namely $X_8$-$X_7$-F-$X_5$-$X_4$-$X_3$-$X_2$-$X_1$ (SEQ ID NO: 52).

In some preferred embodiments, the isolated peptide of the invention has the sequence selected from the group comprising ILFSSFLC (SEQ ID NO: 27); GGMRKFIC (SEQ ID NO: 28); PVVTSFPL (SEQ ID NO: 29); ILFASFLC (SEQ ID NO: 30); GGMRAFIC (SEQ ID NO: 31).

In other preferred embodiments, the isolated peptide of the invention has the sequence selected from the group comprising SEQ ID Nos: 5 to 31, 48, 49 and 50.

In other embodiments, the isolated peptide of the invention further comprises a linker at N- and/or C-terminus, wherein the linker at N- and/or C-terminus is independently selected from the group comprising a linker peptide sequence having a length of at least 3 amino acid residues, a polymer, or a combination thereof. In some preferred embodiments the linker peptide sequence comprises any amino acid residue, preferably any natural L-amino acid residue or is selected from the group comprising poly-Gly and Gly-rich linkers, 16-amino acid Gly-rich linker (GGGGSLVPRGSGGGGS) (SEQ ID NO:1), 6-amino acid Gly-rich linker (GSGSGS) (SEQ ID NO:2), GSGGGTGGGSG (SEQ ID NO:3), PLTG (SEQ ID NO:59), GGGGSGGGGS (SEQ ID NO:60), GGGGS (SEQ ID NO:61), GGGGSGGGGSVSR (SEQ ID NO:62), GGGGSVSR (SEQ ID NO:63), PLTGGGGGSGGGGS (SEQ ID NO:64). In other preferred embodiments, the polymer is selected from the group comprising DSG, DSS, BS3, TSAT (trifunctional), BS(PEG)5, BS(PEG)9, DSP, DTSSP, DST, BSOCOES, EGS, Sulfo-EGS, DMA, DMP, DMS, DTBP, DFDNB, BMOE, BMB, BMH, TMEA (trifunctional), BM(PEG)2, BM(PEG)3, DTME, AMAS, BMPS, GMBS and Sulfo-GMBS, MBS and Sulfo-MBS, SMCC and Sulfo-SMCC, EMCS and Sulfo-EMCS, SMPB and Sulfo-SMPB, SMPH, LC-SMCC, Sulfo-KMUS, SM(PEG)2, SM(PEG)4, SM(PEG)6, SM(PEG)8, SM(PEG)12, SM(PEG)24, SPDP or SPDP, LC-SPDP and Sulfo-LC-SPDP, SMPT, PEG4-SPDP, PEG12-SPDP, SIA, SBAP, SIAB, Sulfo-SIAB, ANB-NOS, Sulfo-SANPAH, ATFB, SDA and Sulfo-SDA, LC-SDA and Sulfo-LC-SDA, SDAD and Sulfo-SDAD, DCC, EDC or EDAC, BMPH, EMCH, MPBH, KMUH, PDPH, PMPI, SPB.

In some embodiments, the linker peptide sequence at N- and/or C-terminus is independently selected from the group comprising GGGGSLVPRGSGGGGS (SEQ ID NO:1), GSGSGS (SEQ ID NO:2), GSGGGTGGGSG (SEQ ID NO:3), PLTG (SEQ ID NO:59), GGGGSGGGGS (SEQ ID NO:60), GGGGS (SEQ ID NO:61), GGGGSGGGGSVSR (SEQ ID NO:62), GGGGSVSR (SEQ ID NO:63), PLTGGGGGSGGGGS (SEQ ID NO:64).

In other embodiment, the linker peptide sequence at N- and/or C-terminus is independently selected from the group comprising GGGGSLVPRGSGGGGS (SEQ ID NO:1), GSGSGS (SEQ ID NO:2), GSGGGTGGGSG (SEQ ID NO:3).

Described linker operably join two peptides/polypeptides of interest such that the expression and activity (for example antibody binding and/or receptor binding) of the polypeptides connected by the linkers are durable and optimal.

The linker described herein refers to a peptide sequence designed to connect (e.g., join, link) two protein sequences, wherein the linker is typically not disposed between the two protein or peptide sequences in nature. In the context of the present invention, the phrase "linked" or "joined" or "connected" generally refers to a functional linkage between two contiguous or adjacent amino acid sequences to produce a polypeptide that generally does not exist in nature. Generally, linked peptides are contiguous or adjacent to one another and retain their respective operability and function when joined. A linker is also referred to as a spacer.

The linker peptide sequence can be of any appropriate length to connect one or more proteins of interest and is preferably designed to be sufficiently flexible so as to allow the proper folding and/or function and/or activity of one or both of the peptides it connects. Thus, the linker peptide can have a length of no more than 3, no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95 or no more than 100 amino acids. In some embodiments, the linker peptide can have a length of at least 3, at least 4, at least 5, at least 6, at least 7, at least 8, at least 9, at least 10, at least 12, at least 15, at least 18, at least 20, at least 25, at least 30, at least 35, at least 40, at least 45, or at least 50 amino acids. In some embodiments, the linker comprises at least 3 and no more than 60 amino acids, at least 3 and no more than 55 amino acids, at least 3 and no more than 50 amino acids, at least 3 and no more than 45 amino acids, at least 3 and no more than 40 amino acids, at least 3 and no more 35 amino acids, at least 3 and no more than 30 amino acids, at least 3 and no more than 25 amino acids, at least 3 and no more than 20 amino acids or at least 3 and no more than 15 amino acids. In certain embodiments, the linker comprises 3 to 20 amino acids, and in particular embodiments, comprises 3 and 4 amino acids. In a polypeptide composition comprising a linker, the 5' end (e.g., terminus) of the linker peptide sequence (for example amino acid sequence) is adjacent to and covalently linked to the 3' end of one protein sequence (for example full-length protein or protein domain, fragment or variant) and, further, the 3' end of the linker amino acid sequence is adjacent to and covalently linked to the 5' end of another protein sequence. Polypeptide compositions produced in this manner are commonly referred to a fusion or chimeric protein/polypeptides and typically are made by the expression (for example transcription, translation) of nucleic acid sequences encoding the polypeptide compositions, in the appropriate system. Means by which to make fusion and/or chimeric polypeptides are well-known in the art (see for example, Sambrook et al., Molecular Cloning: A Laboratory Manual, Cold Springs Harbor Laboratory, 1992) New York which is incorporated by reference herein in its entirety).

In one preferred embodiment, the isolated peptide of the invention comprises at least 15 amino acid residues. In another preferred embodiment, the isolated peptide of the invention comprises 20 amino acid residues.

The term "peptide" in the present invention designate a series of amino acid residues, typically L-amino acids, connected one to the other, typically by peptide bonds between the α-amino and carboxyl groups of adjacent amino acids. The preferred peptides of the invention are 15 or 20 residues in length and usually consist of between 5 and 30 amino acid residues, preferably 8 to 20 amino acid residues. In certain embodiments the size of the at least one peptide of the invention may comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or greater amino acid residues, and any range derivable therein.

An "immunogenic peptide", "immunodominant epitope" or "peptide epitope" is a peptide which comprises an allele-specific motif or supermotif such that the peptide will bind an antiphospholipid antibodies (aPLA) and/or is recognized by CD4+ T cells that are able to induce production of antiphospholipid antibodies (aPLA).

To identify β2GP1-domain-specific T cells in APS patients, PBMC were isolated from 9 APS patients (Table 1), and 3 healthy controls (HC) were stimulated with native 2GP1, reduced β2GP1 and recombinant β2GP1-domain I-II, -domain III-IV and -domain V (FIG. 1A). The proliferation of PBMC was tested by the 5,6-carboxyfluorescein diacetate succinimidyl ester (CFSE) dilution assay. In contrast with HC, CD4+ T cell proliferative responses were detected in primary culture to β2GP1-domain I-II and reduced β2GP1 from APS patients (FIGS. 1B and 1C). While the cryptic epitope exposed by reduced β2GP1 was recognized by β2GP1 reactive T cells in the normal T cell repertoire of APS patients, native β2GP1 was unable to significantly stimulate T cell proliferation (FIG. 1C). The proliferation controls performed with tetanus toxoid (TTx) and CD3-CD28-beads, i.e specific and unspecific T cell proliferation stimuli, showed that the proliferative ability of T cells from HC and APS were unaltered (FIG. 1D). These results suggest that the core sequence(s) of the β2GP1 peptide(s) inducing T cell proliferation were present in $β_2$GP1-domain I-II.

TABLE 1

Clinical and laboratory profiles of the 9 patients providing the aPLA

| | LA | aCL IgG | aβ2GP1 IgC | Clinical manifestions |
|---|---|---|---|---|
| aPLA 1 | + | >100 | POSITIVE | Arterial thrombosis |
| aPLA 2 | + | >60 | POSITIVE | Fetal loss |
| aPLA 3 | ND | >100 | POSITIVE | Venous thrombosis |
| aPLA 4 | + | 30.2 | POSITIVE | Recurrent fetal loss |
| aPLA 5 | ND | >60 | POSITIVE | Arterial thrombosis |
| aPLA 6 | + | 46 | POSITIVE | Arterial thrombosis |
| aPLA 7 | + | >60 | POSITIVE | Fetal loss |
| aPLA 8 | + | >60 | POSITIVE | Fetal loss |
| aPLA 9 | + | >57 | POSITIVE | Thromboembolism | aCL IgG anticardiolipin IgG (normal value < 5 GPL), aβ2GP1 IgG,
ND not done
(patient under vitamin K treatment), >2 fetal loss = Recurrent fetal loss Candidate regions of β2GP1 containing T cell determinants having been identified, proliferative responses of APS patients against a pool of β2GP1 peptides were tested. For this purpose, it was tested the proliferation of PBMC from APS patients and HC to the pools of peptides containing 4 to 5 β2GP1-domain I-II peptides from a library of 13 synthetic overlapping 20-mer peptides present in the 138-amino acid sequence of β2GP1 domain I-II (FIG. 2A). By CFSE dilution assay, proliferative responses in primary cultures to (β2GP1-domain I-II peptide pool III (FIG. 2B) were identified. T cell proliferations of HC and APC triggered by CD3-CD28 have shown similar responses. β2GP1-domain I-II peptide pool III was composed of five peptides consistently insoluble in water with the cryptic character of epitope recognized by γ2GP1 reactive T cell. Interestingly, this pool of peptides contained the region targeted by aPLA, i.e peptide n° 6 (p6).[18] It was then examined the responses to individual $β_2$GP1 peptides contained in pool III. T cell proliferation response against leader peptide n°1 (p1) (SEQ ID NO:32) was significantly increased (but not against peptides n°4; 6; 10 or 11), while T cell proliferations of HC showed a similar response to CD3-CD28 (FIG. 2C). To confirm the presence of circulating T cells specific for p1 (SEQ ID NO:32), the HLA class II haplotype profiles of APS patients used previously (Table 2) was defined. It was then used pMHCII-p1 tetramer DRB3* 02:02 staining to detect specific circulating T cells in 2GP1-domain I-II pulsed T cell population from APS patients. Although, as expected, no population was observed with negative control pMHC-OVA (tetramer with a peptide of ovalbumin) a pMHC-p1 positive population was strongly present in β2GP1-domain I-II specific pulsed T cell population (FIG. 2D). pMHC-TTx staining was used as a positive control (FIG. 2D). These results demonstrated that the immunodominant β2GP1-specific CD4+ T cells' epitope in patients with APS is present in a sequence of amino acids corresponding to MISPVLILF-SSFLCHVAIAG (SEQ ID NO:4), which corresponds to the signal peptide of β2GP1.

TABLE 2

Haplotype profiles of 6 patients from table 1

| | Haplotype | | | | | Clinical manifestations | |
| | | | | | | Pregnancy | |
| | DRB1* | DRB3* | DRB4* | DQB1* | DPB1* | loss | Thrombosis |
|---|---|---|---|---|---|---|---|
| Patient 1 | 04:03/— | | | 03:02/03:05 | 04:01/— | + | − |
| Patient 2 | 09:01/13:01 | 02:02 | 01:03 | 03:02/06:03 | 05:01/14:01 | + | − |
| Patient 3 | 03:01/11:04 | 02:02 | | 02:01/03:01 | 03:01/04:02 | + | + |
| Patient 4 | 04:03/— | | | 03:02/03:05 | 04:01/09:01 | − | + |
| Patient 5 | 01:01/13:01 | 01:01 | | 05:01/06:03 | NT | + | + |
| Patient 6 | 04:01/13:01 | 02:02 | 01:03 | 03:02/06:03 | 04:01/04:02 | − | + |

To identify a potential consensus motif between p1 (SEQ ID NO:32) and p6 (SEQ ID NO:33), which was previously reported containing the aPLA-binding discontinuous epitope R39-R43, their sequences were aligned and observed a common motif present around a phenylalanine. This motif seemed to be determined by intrinsic physical properties (polar and nonpolar) and not by amino acid sequences. To investigate the ability of p1 (SEQ ID NO:32) to interact with patient-derived anti-β2GP1 antibodies and to identify critical residues in the motif, it was generated an alanine scanning library of p1 (SEQ ID NO:32) and p6 (SEQ ID NO:33) including the common motif (data not shown) to perform an ELISA epitope mapping assay. aPLA are able to bind p1 (SEQ ID NO:32) as potently as p6 (SEQ ID NO:33). The mutations I7A, L8A F9A, S11A, F12A and C14A of p1 (SEQ ID NO:32) significantly decreased the binding of aPLA. Similarly, mutations R58A (R39), G59A (G40), G60A (G41), M61A (M42), R62A (R43), F64A and C66A were involved in the binding of aPLA to p6 (SEQ ID NO:33) (data not shown). aPLA interacted similarly with both peptides although the sequences of amino acids present in the motif were not the same. It seems that the aPLA-interacting motif ($X_1$-$X_2$-$X_3$-$X_4$-$X_5$-F-$X_7$-$X_8$) is dependent on polar or nonpolar properties more than hydropathy classes or charge of residues. Alanine is nonpolar but it decreased aPLA ability to bind I7A, L8A, F9A, C14A p1-mutated peptides as well as R58A, G59A, G60A, M61A, C66A p6-mutated peptides. These data suggest that the volume of amino acids and the ability to form electrostatic or hydrogen bonds may also contribute to interactions between aPLA and the motif. Bioinformatical analysis was than performed using Prosite resource (SIB Swiss Institute of Bioinformatics) to find the $X_1$-$X_2$-$X_3$-$X_4$-$X_5$-F-$X_7$-$X_8$ motif (N- to C-term) (SEQ ID NO:51) but also the $X_8$-$X_7$-F-$X_5$-$X_4$-$X_3$-$X_2$-$X_1$ motif which is the reverse motif (C- to N-term) (SEQ ID NO:52) in the human proteome. Four sequences were present in domain I of β2GP1; two $X_1$-$X_2$-$X_3$-$X_4$-$X_5$-F-$X_7$-C motifs (SEQ ID NO:53) and two $X_8$-$X_7$-F-$X_5$-$X_4$-$X_3$-$X_2$-$X_1$ motifs (SEQ ID NO:52) (Table 3). $X_8$-$X_7$-F-$X_5$-$X_4$-$X_3$-$X_2$-$X_1$ motifs (SEQ ID NO:52) were present in p1 (SEQ ID NO:32) and p3 (SEQ ID NO:39 and SEQ ID NO:34). It was thus assessed the ability of aPLA to interact with p3 (SEQ ID NO:39). A slightly different motif was included, that was present in p4 (SEQ ID NO:35) to investigate whether a degenerated motif was able to interact with aPLA. As expected, aPLA bound to p3 with a similar efficiency compared to p1 (SEQ ID NO:32) and p6 (SEQ ID NO:33) (FIG. 3). It was further observed that p4 (SEQ ID NO:35), although less potent to interact with aPLA, significantly bound to them (FIG. 3). Altogether, these data demonstrated that aPLA interact with a $X_1$-$X_2$-$X_3$-$X_4$-$X_5$-F-$X_7$-C motif (SEQ ID NO:53), and more generally with a $X_1$-$X_2$-$X_3$-$X_4$-$X_5$-F-$X_7$-$X_8$ motif (SEQ ID NO:51), in which the polarity of the residues was more important than the hydropathy classes. This motif could also interact with aPLA even if the motif was slightly modified by insertion or deletion of an amino acid before or after the key phenylalanine residue. Finally, aPLA were able to bind motifs in sense or anti-senses.

TABLE 3

Different motifs present in aPLA-related receptors and proteins

| Names and References | Localization | Number | Orientation |
|---|---|---|---|
| Motif | $X_1$-$X_2$-$X_3$-$X_4$-$X_5$-F-$X_7$-C (SEQ ID NO: 53) | | |
| aPLA- | β2GP1[31] Domain I | 2 | NH$_2$ => COOH |
| related | TLR2[32] Extracellular | 1 | |
| receptors | ApoER2[33] Extracellular | 2 | |
| Motif | $X_1$-$X_2$-$X_3$-$X_4$-$X_5$-F-$X_7$-$X_8$ (SEQ ID NO: 51) | | |
| aPLA- | β2GP1[31] Domain I | 2 | COOH => NH$_2$ |
| related | TLR8[34] Extracellular | 1 | |
| receptors | ANXA2[35] Annexin repeats | 1 | |
| Motif | $X_1$-$X_2$-$X_3$-$X_4$-F-$X_7$-$X_8$ (SEQ ID NO: 54) | | |
| aPLA- | β2GP1[31] Domain III | 1 | COOH => NH$_2$ |
| related | TLR1[16] Extracellular | 1 | |
| receptors | TLR4[36] Extracellular | 3 | |
| | TLR6[16] Extracellular | 1 | |
| | TLR7[37] Extracellular | 2 | |
| | TLR9[38] Extracellular | 2 | |
| Motif | $X_1$-$X_2$-$X_3$-$X_4$-$X_5$-NPaa-F-$X_7$-$X_8$ (NPaa: non-polar amino acid residue) (SEQ ID NO:55) | | |
| aPLA- | GPIbα[39] Extracellular | 1 | COOH => NH$_2$ |
| related receptors | | | |

Vlachoyiannopoulos et al.,[19] identified a consensus motif between CD40 and p3 able of interacting with aPLA. Although this sequence had one additional nonpolar amino acid between the couple of amino acids, polar and phenylalanine ($X_5$-$X_7$-F-NPaa-$X_5$-$X_4$-$X_3$-$X_2$-$X_1$, NPaa=non-polar amino acid residue) (SEQ ID NO:56), it was strongly related to the initial motif. In addition, it seemed that both polar amino acids present in the $X_1$-$X_2$-$X_3$-$X_4$-$X_5$-F-$X_7$-$X_8$ motif (SEQ ID NO:51) were not fully required (data not shown). Thus additional bioinformatical analysis relative to $X_8$-$X_7$-F-$X_4$-$X_3$-$X_2$-$X_1$ (SEQ ID NO:52) and $X_8$-$X_7$-F-NPaa-$X_5$-$X_4$-$X_3$-$X_2$—$X_1$ motifs (SEQ ID NO:56) was performed. Among the proteins containing these motifs, β2GP1 domain I, TLR1, TLR4, TLR6, TLR7, TLR8, TLR9 and GPIbα were identified (Table 3). In addition to identified proteins containing the motifs $X_1$-$X_2$-$X_3$-$X_4$-$X_5$-F-$X_7$-$X_8$ (SEQ ID NO:51) and $X_8$-$X_7$-F-$X_5$-$X_4$-$X_3$-$X_2$-$X_1$ (SEQ ID NO:52), all potential aPLA-receptors described in the literature possess at least one of these two motifs. These results suggest that $X_1$-$X_2$-$X_3$-$X_4$-$X_5$-F-$X_7$—C(SEQ ID NO:53) and other closely related motifs constitute the potential links between controversial data obtained by different research groups working on aPLA.

Figure 4A:
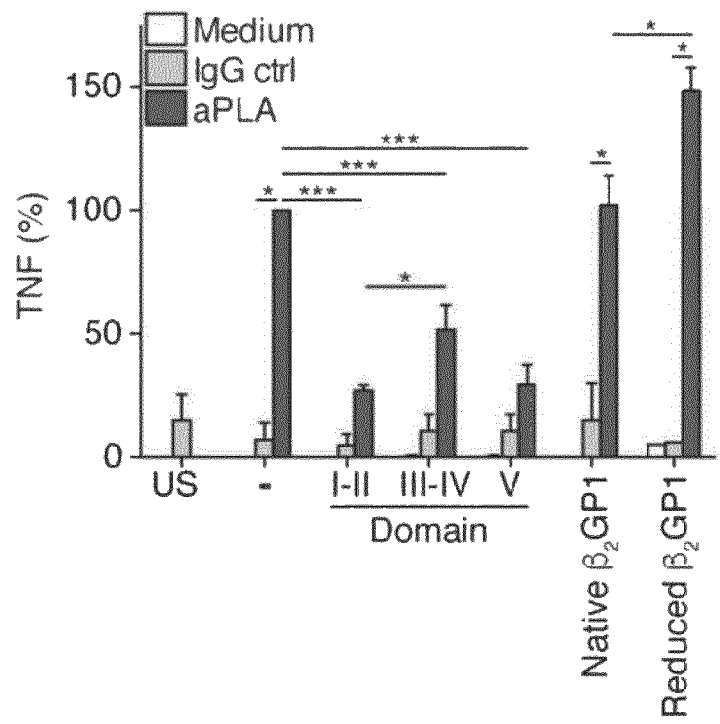
FIG. 4 shows motif containing domains and peptides inhibits aPLA activity. (A) Inhibition of TNF production induced by aPLA by domains I-II, III-IV, V, β2GP1 of reduced β2GP1. (B) Representative picture of IgG ctl (control) or aPLA binding to domains I-II, III-IV, V and β2GP1-coated well. Quantification of aPLA binding to domains I-II, III-IV, V or β2GP1-coated well. aPLA to well coated with domains I-II, III-IV, V, β2GP1 of reduced β2GP1. (C) Inhibition by domain I-II (SEQ ID NO:37), p1 (SEQ ID NO:32), p4 (SEQ ID NO:35), p6 (SEQ ID NO:33), p10 (SEQ ID NO:44) and p11 (SEQ ID NO:45) of TNF production induced by aPLA. (D) Representative picture of IgG ctl (control) or aPLA binding to domains I-II-, p1-, p4-, p6-, p10- and p11-coated well. Quantification of aPLA binding to domains I-II, p1, p4, p6, p10 and p11-coated well. aPLA to well coated with domains I-II, III-IV, V, β2GP1 of reduced β2GP1. Data are mean±SEM of 9 different donors. Statistical significance was determined by Mann-Whitney U analysis.
Figure 4B:
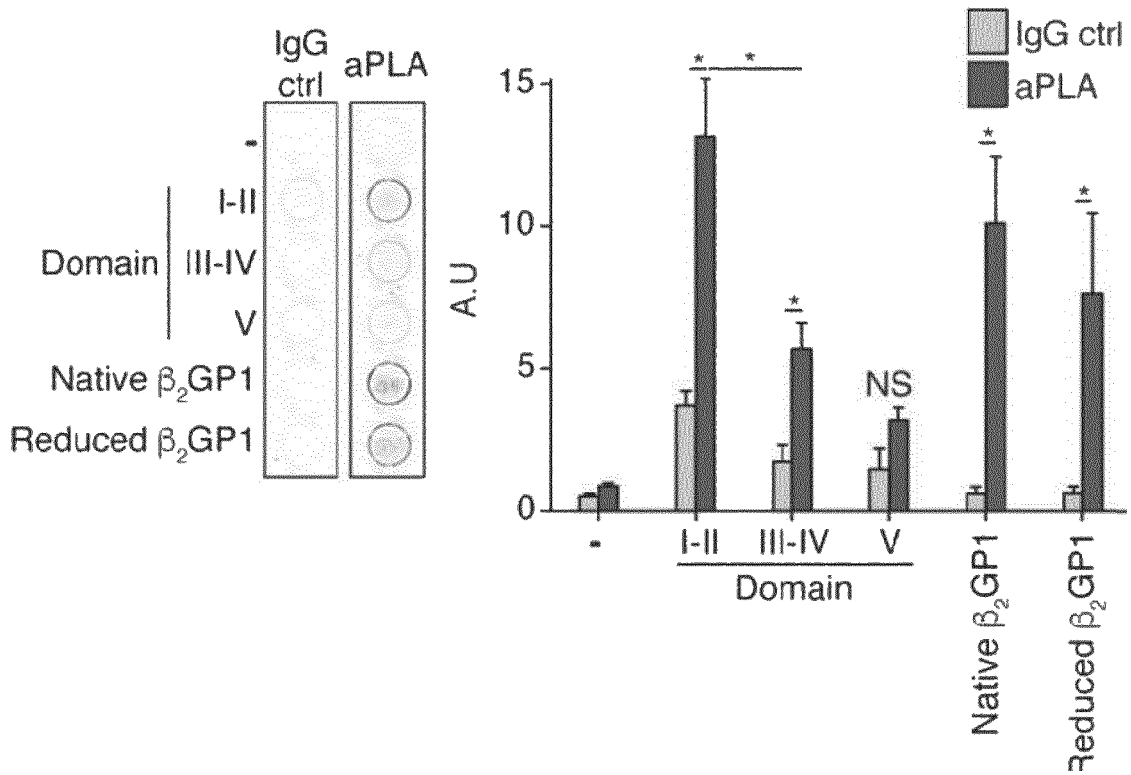
Figure 4C:
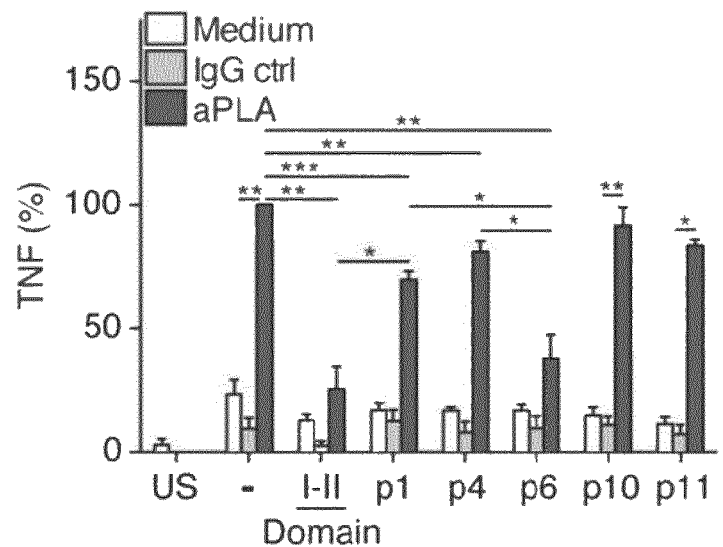
Figure 4D:
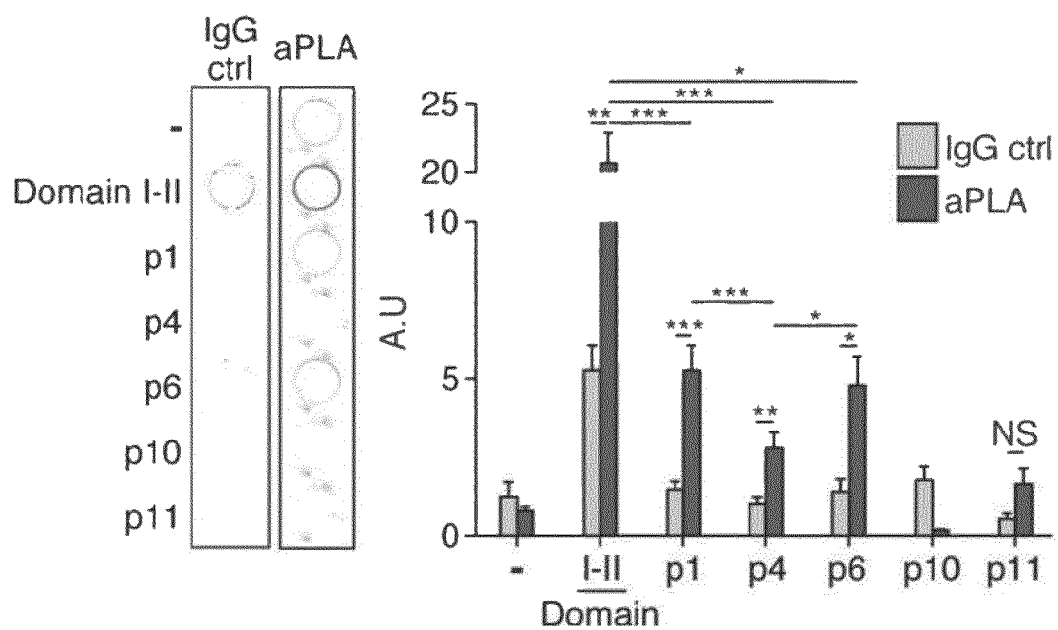

To examine the functional ability of recombinant domains of β2GP1, p1 (SEQ ID NO:32), p4 (SEQ ID NO:35) and p6 (SEQ ID NO:33) to inhibit the activity of aPLA isolated from APS patients studied in experiments presented herein (Table 1), it was evaluated TNF production in human monocytes activated with aPLA that had been treated previously with peptides or recombinant domains. While incubation of human monocytes with aPLA pretreated with β2GP1 and reduced β2GP1 have no effect on aPLA activity, incubation of the aPLA with domain I-II, domain III-IV and domain V significantly decreased the production of TNF induced by aPLA (FIG. 4A). This inhibition of TNF production involved the binding of aPLA onto β2GP1, reduced β2GP1, domain I-II and domain III but not domain V (FIG. 4B). Similarly, pre-incubation with peptides n°1, 4 and 6 (p1, p4 and p6) diminished the production of TNF induced by aPLA, whereas p10 (SEQ ID NO:44) and p11 (SEQ ID NO:45) had no effect (FIG. 4C). This inhibition involved that p1, p4 and p6, but not p10 or p11, interact with aPLA (FIG. 4D). We observed that p1 and p6 had similar aPLA-binding activity, while p4 was significantly less potent to interact with aPLA (FIG. 4D). These results were consistent with the presence of four aPLA-interaction motifs in domain I-II, while p1 and p6 had only one motif (considering that p1 (SEQ ID NO: 32) and revp1 (SEQ ID NO:48) were not simultaneously available). As shown in FIG. 3, the interaction of p4 with aPLA was less effective due to a slightly degenerated motif (FIGS. 4D and 3A). Taken together the results presented herein clearly revealed that the motifs recognized by aPLA, which were present in p1, p4 and p6, but not in p10 or p11, were able to functionally decrease the activity of aPLA. They further demonstrated that the aPLA-interacting motif ($X_8$-$X_7$-F-$X_4$-$X_3$-$X_2$-$X_1$) (SEQ ID NO:58) present in domain III-IV (Table 3) efficiently interacted with aPLA and inhibited its activity, although to a lesser extent than domain I-II (SEQ ID NO:37) (FIG. 4B), confirming the potential targets exposed in Table 3.

The present disclosure deals with the T cell response associated with the production of autoantibodies against β2GP1 and their related epitopes in APS patients. It has been established that the β2GP1 signal peptide (p1) induced the proliferation of CD4+ T cells from APS patients but not from healthy donors. Furthermore, autoreactive CD4+ T cells were detected in APS patient blood samples and bound HLA-DRB3* 02:02 tetramer loaded with p1, thus endorsing the fact that specific HLA-DR alleles are associated with susceptibility to APS.[10, 20, 21] It has been further observed that the signal peptide contained a motif that was similar to that of the R39-R43 epitope. It has been thus identified aPLA-interacting motif ($X_1$-$X_2$-$X_3$-$X_4$-$X_5$-F-$X_7$-$X_8$) (SEQ ID NO:51) dependent on polar or nonpolar properties more than on hydropathy classes of amino acids. The recombinant domains of β2GP1, as well as individual peptides containing this motif, or closely related motifs, were able to inhibit the activity of aPLA on human monocytes. This disclosure provides an attractive explanation for the controversial results obtained on potential aPLA-associated receptors. $X_1$-$X_2$-$X_3$-$X_4$-$X_5$-F-$X_7$—C(SEQ ID NO:53) and $X_1$-$X_2$-$X_3$-$X_4$-$X_5$-F-$X_7$-$X_8$-related motifs (SEQ ID NO:51) are indeed present in all aPLA-associated receptors described in the literature[13] (Table 3). Bioinformatics analyses have however revealed that $X_1$-$X_2$-$X_3$-$X_4$-$X_5$-F-$X_7$-C motif (SEQ ID NO:53) is present and accessible in 16 different proteins within the whole human proteome (Table 4).

TABLE 4

| Accession Number | Protein Name | Gene Name | Sequence | SEQ ID NOs |
|---|---|---|---|---|
| O60603 | Toll-like receptor 2 | TLR2 | AGGNNFIC | 5 |
| O75581 | Low-density lipoprotein receptor-related protein 6 | LRP6 | CLIDQFRC | 6 |
| Q9NR97 | Toll-like receptor 8 | TLR8 | GVLYNFEL | 7 |
| O94813 | Slit homolog 2 protein | SLIT2 | VAIQDFTC | 8 |
| P02749 | Beta-2-glycoprotein 1 | APOH | ILFSSFLC<br>GGMRKFIC<br>PVVTSFPL<br>CLFSSFLI | 9<br>10<br>11<br>12 |
| P04275 | von Willebrand factor | VWF | PPLHDFYC | 13 |
| P10643 | Complement component C7 | C7 | GCGERFRC | 14 |
| P98155 | Very low-density lipoprotein receptor | VLDLR | CGAHEFQC | 15 |
| P98160 | Basement membrane-specific heparan sulfate proteoglycan core protein | HSPG2 | CGPTQFRC | 16 |
| P98164 | Low-density lipoprotein receptor-related protein 2 | LRP2 | CGGYQFTC | 17 |
| Q07954 | Prolow-density lipoprotein receptor-related protein 1 | LRP1 | CLADEFKC<br>CPPHEFKC | 18<br>19 |
| Q13705 | Activin receptor type-2B | ACVR2B | CWLDDFNC | 20 |
| Q14114 | Low-density lipoprotein receptor-related protein 8 | LRP8 | CAPHEFQC<br>CGPREFRC | 21<br>22 |
| Q9BXB4 | Oxysterol-binding protein-related protein 11 | OSBPL11 | IIGETFHC | 23 |

TABLE 4-continued

| Accession Number | Protein Name | Gene Name | Sequence | SEQ ID NOs |
|---|---|---|---|---|
| Q9BZF1 | Oxysterol-binding protein-related protein 8 | OSBPL8 | ILGETFRC | 24 |
| Q9H244 | P2Y purinoceptor 12 | P2RY12 | GPLRTFVC | 25 |
| Q9NPF0 | CD320 antigen | CD320 | CPPTKFQC | 26 |

Although it is well accepted that the β2GP1 domain I is the target of aPLA, the exact sequence of the epitope remains largely unknown. Here, it has been identified $X_1$-$X_2$-$X_3$-$X_4$-$X_5$-F-$X_7$-$X_8$ (SEQ ID NO:51) as being a common aPLA-interacting motif. While the signal peptide (p1), containing an aPLA-interacting motif, was not present in the mature β2GP1, CD4$^+$ T cells were able to recognize the p1 sequence. This suggests that a signal peptide could trigger autoimmune responses. Consistently, it was shown that a polymorphism in the signal peptide of the cytotoxic T-lymphocyte antigen 4 (CTLA-4) leads to autoimmune predispositions.[22] Interestingly, the aPLA-interacting motif present in p1 was also present in revp1, corresponding to a palindromic form of p1. Furthermore, APS patient autoreactive T cell proliferation was triggered by p1 (FIGS. 2C and 2D). Smith et al.,[23] suggested that complementary sequences of proteins may have a function in the induction of autoimmunity. This theory was confirmed by the discovery that autoimmunity can be initiated through an immune response against a peptide that is antisense or complementary to the autoantigen, which then induced anti-idiotypic antibodies (autoantibodies) that cross-reacted with the autoantigen.[24] Furthermore, as a potential origin of APS pathogenicity, the palindromic sequence of p1 could explain the aPLA interactions with p3 and domain III in which the binding sequences were antisense. Six sense and antisense epitopes are present in β2GP1. Five of these are found in domain I (Table 3) and could be the reason for its identification as the main interacting protein of aPLA.

To address the question of aPLA binding epitopes, several research groups performed epitope mapping using point mutations of domain I.[6, 7] They identified D8, D9, K19, S38, R39, G40, M42, R43 and T50 as residues participating in (or contributing to) aPLA-domain I interactions. While 44% of these mutations were present in β2GP1 domain I motifs, the proportion increased to 100% if the mutations directly adjacent to motifs were included. Furthermore the adjacent mutations were at the same position as the motifs.[6, 7] While additional investigations are required in order to define in further detail the exact sequence required to attain the highest affinity for aPLA, these parallels suggest that the motifs proposed could be slightly larger than those exposed in the present study. Another research group highlighted a sequence homology between residues 239-245 of CD40 and residues 26-32 of β2GP1.[19] Residues 26-32 of β2GP1 corresponded to p3 and belonged to the $X_1$-$X_2$-$X_3$-$X_4$-$X_5$ (SEQ ID NO:57) part of the $X_1$-$X_2$—$X_3$-$X_4$-$X_5$-NPaa-F-$X_7$-$X_8$ motif (SEQ ID NO:55) (FIGS. 3 and 5). Mice immunized with a panel of microbial preparations have been shown to produce high titers of anti-β2GP1 antibodies. This panel of bacteria is composed of six different preparations among which *Streptococcus pneumonia*, *Shigella dysenteriae* or *Haemophilus influenzae*.[26] Employing bioinformatical analysis (Prosite resource SIB), it has been found that all bacteria strains used in different preparations carry the $X_1$-$X_2$-$X_3$-$X_4$-$X_5$-F-$X_7$-C motif (SEQ ID NO:53). Not only the bacteria strains but also virus strains carry the $X_1$-$X_2$-$X_3$-$X_4$-$X_5$-F-$X_7$-C motif (SEQ ID NO:53). Several cases or clinical studies including patients with established APS or APS with thromboembolic phenomena have revealed a correlation between increased aPLA levels and HIV, Epstein-Barr virus, hepatitis C virus or herpesvirus-6 infection.[27-30] The bioinformatical analysis has revealed that all these virus strains carry the $X_1$-$X_2$-$X_3$-$X_4$-$X_5$-F-$X_7$-C motif (SEQ ID NO:53). Taken together these data demonstrate that the aPLA-interaction motif $X_1$-$X_2$-$X_3$-$X_4$-$X_5$-F-$X_7$-C(SEQ ID NO:53), and by extension $X_1$-$X_2$-$X_3$-$X_4$-$X_5$-F-$X_7$-$X_8$-related motifs (SEQ ID NO:51) characterized in the present disclosure were strongly related to other previously depicted epitopes, thereby putting emphasis on polarity properties of residues and not on particular sequences.

The characterization of the aPLA epitope performed here leads to a better understanding of the surprising number of candidate receptors described for aPLA.[13] It has been herein shown that all TLRs suggested as aPLA receptors carry at least one motif in their extracellular region. Thus, TLR2 has one $X_1$-$X_2$-$X_3$-$X_4$-$X_5$-F-$X_7$-C motif (SEQ ID NO:53) and TLR4 three $X_1$-$X_2$-$X_3$-$X_4$-F-$X_7$-$X_8$ motifs (SEQ ID NO:51). As presented in FIG. 4D, the $X_1$-$X_2$-$X_3$-$X_4$-$X_5$-F-$X_7$-C motif (SEQ ID NO:53) may be more potent than the $X_1$-$X_2$-$X_3$-$X_4$-F-$X_7$-$X_8$ motif (SEQ ID NO:54) to bind aPLA, but the presence to three $X_1$-$X_2$-$X_3$-$X_4$-F-$X_7$-$X_8$ motifs (SEQ ID NO:54) on TLR4 may explain that TLR2 and TLR4 were proposed as aPLA receptors. Annexin A2, ApoER2 and GPIbα have also at least one motif accessible by aPLA (Table 3). The most described aPLA-interacting protein, 2GP1, has no less than five motifs present mainly in domain I but also in domain III. Several other targets carrying $X_1$-$X_2$-$X_3$-$X_4$-$X_5$-F-$X_7$-$X_8$ motifs (SEQ ID NO:51) are important for APS such as proteins involved in coagulation processes. Thus, thrombin, proteinase-activated receptor 2 (PAR-2 and 3) and the complement C5, C4a or C4b are some of aPLA-targeted proteins carrying $X_1$-$X_2$-$X_3$-$X_4$-$X_5$-F-$X_7$-$X_8$ motifs (SEQ ID NO:51) (data not shown).

The present invention provides the opportunity to provide an accurate tool for the detection of aPLA, specifically β2GP1 antibodies for diagnostic purposes. Furthermore, aPLA-interacting motifs present in peptides have the ability to inhibit aPLA activity and represent a prevention strategy for APS instead of anticoagulants. Finally, compositions containing the peptides of the invention associated with inducers of cell death can be used to specifically disrupt autoreactive T cells in APS patients, thus providing an excellent therapeutic approach.

According to another aspect of the invention, the peptides of the invention are loaded on class II MHC molecules to provide a MHC composition for diagnosing and/or treating the antiphospholipid syndrome (APS). Thus the present invention also provides a MHC composition comprising MHC class II molecules and the peptide of the invention.

In an embodiment of the invention, the MHC composition further comprises an inducer of cell death. In an additional embodiment of the MHC composition of the invention, the inducer of cell death is associated to streptavidine and MHC class II molecules are further modified by binding moieties such as biotin. In another additional embodiment, the inducer of cell death is selected from the group comprising doxorubicin, epirubicin, idarubicin, mitoxantrone, bleomycin, bortezomib, cyclophosphamide, the type I ribosome-inactivating protein saporin and oxaliplatin.

In a preferred embodiment of the MHC composition of the invention, the MHC class II molecules are tetramers or dextramers. In another preferred embodiment of the MHC invention, the composition is a soluble composition. In a further preferred embodiment, the MHC composition of the invention is attached to an insoluble carrier or a substrate.

The term "major histocompatibility antigen" refers to molecules belonging to the HLA system in man (H2 in the mouse), which are divided in two general classes. MHC class I molecules are made of a single polymorphic chain containing 3 domains (alpha 1, 2 and 3), which associates with beta 2 microglobulin at cell surface. Class I molecules are encoded by 3 loci, called A, B and C in humans. Such molecules present peptides to T lymphocytes of the CD8+ subset. "Class II molecules" as occurring on cells are transmembrane proteins consisting of 2 polymorphic chains, each containing 2 chains (alpha 1 and 2, and beta 1 and 2). These class II molecules are encoded by 3 loci, DP, DQ and DR in man. For the purpose of the present invention it is required and sufficient that the "MHC molecule—peptide of the invention" complex can bind to a CD4+ T cell.

In one embodiment, cells presenting the relevant MHC class II molecule are incubated with the peptide of the invention. The cells are then used as such to bind the cognate TCR, either in soluble phase followed by facs analysis, or after insolubilisation on plates or on beads. These techniques are well described in the art. In an alternative embodiment, cells are lysed and the MHC class II molecules loaded with peptide of the invention are prepared by, for instance, chromatography. The MHC-peptide compositions, with or without labelling, can then be used in soluble phase to interact with a population of CD4+ T cells, or insolubilized on plates or beads or any suitable solid-phase support for the detection of CD4+ T cells.

In another embodiment, MHC class II molecules are produced by cDNA technology using cell transfection or transduction. The cDNA construct can contain the full-length class II molecule with its intramembranous sequences for surface anchoring and use of cells as described above, or without the intramembranous sequence for secretion. Such secreted class II molecules can be purified and used as described above, in soluble forms or after insolubilisation on a solid surface such as plates or beads.

The MHC molecules can be further modified by binding moieties (peptide tags such as His tag, a binding moiety such as biotin, binding proteins such as GST, MBP, antibody tags such as HA tags). The MHC molecules can also be modified with detectable labels such as chromophoric groups, radio-active labels, magnetic beads.

In yet another embodiment, the cDNA construct encompassing class II MHC molecules also comprises the sequence of the peptide of the invention, so that the engineered molecule constitutively expresses the peptide of the invention in fusion with the MHC molecule. It is advantageous in this embodiment that the peptide of the invention comprises a linker, which is in between the sequence of class II molecule and the sequence of the peptide of the invention, so as to allow proper folding and presentation of the peptide of the invention into the cleft of the class II molecule. These linkers are typically a polypeptide sequence of 3 to 15 amino acids with serines and/or glycines to provide enough flexibility for the epitope to tether on the beta chains. The linker can further comprise a protease specific recognition site (e.g. for thrombin) such that after expression and folding, the peptide is presented in its normal configuration.

Soluble forms of MHC class II molecules before or after loading with a peptide of the invention can be used in the form of dimers or polymers, either by reacting several molecules between each other or by insolubilizing such molecules onto a solid phase such as beads or plates. These methods are described in the art. MHC molecules can occur as multimers, such as tetramers or dextramers.

Peptides of the invention can be generated using recombinant DNA techniques, in bacteria, yeast, insect cells, plant cells or mammalian cells. Peptides of limited length, can be prepared by chemical peptide synthesis, wherein peptides are prepared by coupling the different amino acids to each other. Chemical synthesis is particularly suitable for the inclusion of for example D-amino acids, amino acids with non-naturally occurring side chains or natural amino acids with modified side chains such as methylated cysteine.

Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry. During peptide synthesis several protecting groups are used. For example hydroxyl and carboxyl functionalities are protected by t-butyl group, Lysine and tryptophan are protected by t-Boc group, and asparagine, glutamine, cysteine and histidine are protected by trityl group, and arginine is protected by the pbf group. In particular embodiments, such protecting groups can be left on the peptide after synthesis.

Alternatively, the peptides, and especially fusion proteins of peptide and MHC molecule can be synthesized by using nucleic acid molecules which encode the peptides of this invention in an appropriate expression vector which include the encoding nucleotide sequences. Such DNA molecules may be readily prepared using an automated DNA synthesizer and the well-known codon-amino acid relationship of the genetic code. Such a DNA molecule also may be obtained as genomic DNA or as cDNA using oligonucleotide probes and conventional hybridization methodologies. Such DNA molecules may be incorporated into expression vectors, including plasmids, which are adapted for the expression of the DNA and production of the polypeptide in a suitable host such as bacterium, for example *Escherichia coli*, yeast cell, animal cell or plant cell.

The physical and chemical properties of a peptide of interest (such as solubility, stability) are examined to determine whether the peptide is/would be suitable for use for applications as defined for the present invention. Typically this is optimised by adjusting the sequence of the peptide. Optionally, the peptide can be modified after synthesis (chemical modifications such as adding/deleting functional groups) using techniques known in the art.

Another aspect of the invention provides a pharmaceutical composition comprising the peptide of the invention in an amount effective to prevent, reduce or inhibit one or more symptoms of the antiphospholipid syndrome (APS) in a subject in need thereof, and a pharmaceutically acceptable carrier for administration of the peptide.

Pharmaceutical compositions for delivering peptides are well known in the art. Such compositions typically contain drug carriers based on organic materials. In addition, different methods are known for polymer-peptide conjugation before being followed by physical encapsulation techniques, which is divided into surfactant-based techniques and polymer carriers. Surfactant-based techniques are dominated by liposome, microemulsions and solid-lipid nanoparticles. The field widens further in the polymer field. The delivery of peptides has been enhanced using polymer-decorated liposomes, solid microspheres, polyelectrolyte complex, emulsions, hydrogels, and injectable polymers.

Another aspect of the invention provides a method for treating the antiphospholipid syndrome (APS) in a subject comprising administering to said subject a therapeutically effective amount of the MHC composition of the invention.

A further aspect of the invention provides the MHC composition of the invention for use in treatment of the antiphospholipid syndrome (APS).

A "therapeutically effective amount" or "effective amount" of the peptide of the present invention and the MHC composition of the present invention preferably results in a decrease in severity of disease symptoms, an increase in frequency and duration of disease symptom-free periods, an increase in lifepan, disease remission, or a prevention or reduction of impairment or disability due to the disease affliction. One of ordinary skill in the art would be able to determine a therapeutically effective amount based on such factors as the subject's size, the severity of the subject's symptoms, and the particular composition or route of administration selected.

Another aspect of the invention provides a method for preventing and/or inhibiting one or more symptoms of the antiphospholipid syndrome (APS) in a subject comprising administering to said subject a therapeutically effect amount of the peptide of the invention or the pharmaceutical composition of the invention.

A further aspect of the invention provides the peptide of the invention for use in a method for preventing and/or inhibiting one or more symptoms of the antiphospholipid syndrome (APS).

The invention also provides a use of the peptide of the invention for the manufacturing of a medicament for treatment and/or prevention of the antiphospholipid syndrome (APS).

Another aspect of the invention provides a method for diagnosing of an antiphospholipid syndrome (APS) in a subject, wherein presence or absence of an antiphospholipid antibody (aPLA) is detected in a sample from the subject diagnosed, and wherein the presence of an antiphospholipid antibody is indicative of the APS disease and wherein the antiphospholipid antibody is detected using an immunoassay comprising the steps of
(i) providing a sample;
(ii) contacting the sample with the peptide of the invention under conditions allowing for the formation of a complex between antiphospholipid antibodies with the peptide of the invention;
(iii) detecting the complex.

In the method for diagnosing, the peptide is preferably immobilized on a surface or on beads and/or the complex is preferably detected using a secondary antibody against the Fc portion of the antiphospholipid, wherein preferably the antiphospholipid antibody is an IgG-antibody and the secondary antibody is an anti-IgG antibody, and/or the secondary antibody is preferably labelled with a detectable marker. In preferred embodiments, the immunoassay is selected from the group of immunoprecipitation, enzyme immunoassay (EIA), radioimmunoassay (RIA) or fluorescence immunoassay, a chemilumineszent assay, an agglutination assay, nephelometric assay, turbidimetric assay, a Western blot, a competitive immunoassay, a non-competitive immunoassay, a homogeneous immunoassay a heterogeneous immunoassay, a bioassay and a reporter-assay such as a Luciferase-Assay. Preferably, the immunoassay is an ELISA.

Another aspect of the invention provides a method for detecting the presence of antiphospholipid antibody in a sample comprising
(i) providing a sample,
(i) contacting the sample with the peptide of the invention under conditions allowing for the formation of a complex between antiphospholipid antibodies with the peptide of the invention;
(iii) detecting the complex using an immunoassay.

In the method for diagnosing, the peptide is preferably immobilized on a surface or on beads and/or the complex is preferably detected using a secondary antibody against the Fc portion of the antiphospholipid, wherein preferably the antiphospholipid antibody is an IgG-antibody and the secondary antibody is an anti-IgG antibody, and/or the secondary antibody is preferably labelled with a detectable marker. In preferred embodiments, the immunoassay is selected from the group of immunoprecipitation, enzyme immunoassay (EIA), radioimmunoassay (RIA) or fluorescence immunoassay, a chemilumineszent assay, an agglutination assay, nephelometric assay, turbidimetric assay, a Western blot, a competitive immunoassay, a non-competitive immunoassay, a homogeneous immunoassay a heterogeneous immunoassay, a bioassay and a reporter-assay such as a Luciferase-Assay. Preferably, the immunoassay is an ELISA.

The invention also encompasses a diagnostic immunoassay for determining the presence of aPL antibody in a sample (such as body fluids) taken from subjects suspected of suffering from an aPL antibody-mediated disease comprising contacting a sample of a body fluid with a peptide of the invention which specifically binds aPL antibodies and determining by methods well known in the art whether aPL antibodies are present in the sample and, if present, quantitating the amount of aPL antibodies present in the sample. One such immunoassay comprises: (a) coating wells of a microtitration plate with a peptide of the invention which specifically binds aPL antibodies; (b) washing the wells to wash away unbound peptide; (c) adding a test sample of a sample obtained from a subject to the wells wash away unbound peptide; (d) adding a test sample of a sample obtained from a subject to the wells and incubating for a pre-determined time; (e) washing the wells to remove unbound test sample; (f) adding anti-human IgG conjugated with a label to the wells of the plate and incubating for a pre-determined time; (g) washing the wells to wash away unbound anti-human IgG conjugate; (h) adding a substrate for the labelled conjugate and developing the substrate/label reaction for a pre-determined time; (i) measuring the end-product of the substrate/label reaction to determine the presence of anti-aPL antibody in the test sample. A diagnostic immunoassay as described above wherein the immunoassay is quantitative is also encompassed.

Another aspect of the invention provides a use of the peptide of the invention for detecting antiphospholipid antibodies.

A further aspect of the invention provides a method for diagnosing of an antiphospholipid syndrome (APS) in a subject, wherein presence or absence of CD4+ T cells, able to induce production of antiphospholipid antibodies, is detected in a sample from the subject diagnosed, and wherein the presence of said CD4+ T cells is indicative of the APS disease, comprising the steps of (i) providing a sample;
(ii) contacting the sample with the MHC composition of the invention;
(iii) detecting CD4+ T cells by measuring the binding of said composition with CD4+ T cells in said sample, wherein the binding of the composition to a CD4+ T cell is indicative for the presence of CD4+ T cells in said sample.

In some preferred embodiments, the method further comprises the step of isolating the CD4+ T cells bound to said composition, and/or the sample is a blood sample.

Another aspect of the invention provides a use of a MHC composition of the invention for the detection, preparation or depletion of CD4+ T cells.

Likewise the invention relates to a method of treating APS comprising diagnosis of APS with a diagnostic method according to the invention, and administering a MHC composition according to the invention to the subject upon a result being indicative of APS in said diagnostic method.

A sample for use in the methods for diagnosing of the invention may be derived from different sources. It is understood that a "sample" as contemplated herein includes also a sample that is modified from its original state, for example, by purification, dilution or the addition of any other component or components, such as the addition of chemical or biochemical substances to the solution, such as acids, bases, buffers, salts, solvents, reactive dyes, detergents, emulsifiers, chelators. The sample is preferably a biological sample, such as body fluid sample. Non-limiting examples of biological samples include whole blood or a component thereof (e.g. plasma, serum), urine, saliva lymph, bile fluid, sputum, tears, cerebrospinal fluid, bronchioalveolar lavage fluid, synovial fluid, semen, ascitic tumour fluid, breast milk and pus. The biological sample may be derived from a healthy individual, or an individual suffering from a particular disease or condition, such as antiphospholipid syndrome (APS). For example, the individual may be suffering from or suspected to be suffering from an autoimmune disease, such as antiphospholipid syndrome (APS). The biological sample may be collected from a subject and used directly. Alternatively, the biological sample may be processed prior to use. For example, the biological sample may be purified, concentrated, separated into various components, or otherwise modified prior to use. It will be understood that a biological sample as contemplated herein includes cultured biological materials, including a sample derived from cultured cells, such as culture medium collected from cultured cells or a cell pellet. Accordingly, a biological sample may refer to a lysate, homogenate or extract prepared from a whole organism or a subset of its tissues, cells or component parts, or a fraction or portion thereof. A biological sample may also be modified prior to use, for example, by purification of one or more components, dilution, and/or centrifugation.

Another aspect of the invention provides a kit for detecting in a sample the presence or absence of an antiphospholipid antibody, the kit comprising the peptide of the invention.

A further aspect of the invention provides a kit for detecting in a sample the presence or absence of CD4+ T cells able to induce production of antiphospholipid antibodies, the kit comprising the MHC composition of the invention.

The invention provides kits for detecting in a sample the presence or absence of an antiphospholipid antibody or the presence or absence of CD4+ T cells able to induce production of antiphospholipid antibodies. The kits thus comprise peptides of the invention or the MHC compositions of the invention. The kits may be used for the diagnosis or prognosis of an autoimmune disease, such as APS, in a subject.

Kits of the invention may include other components required to conduct the methods of the present invention, such as buffers and/or diluents. The kits may comprise one or more means for obtaining a sample from a subject. The kits typically include containers for housing the various components and instructions for using the kit components in the methods of the invention. Kits of the invention may comprise a suitable support on which one or more reagents are immobilised or may be immobilised, for example, kits of the invention may comprise a support coated with an antibody, strepavidin, or biotin. Non-limiting examples of suitable supports include assay plates (e.g. micro titer plates) or test tubes manufactured from polyethylene, polypropylene, polystyrene, Sephadex, polyvinyl chloride, plastic beads, and, as well as particulate materials such as filter paper, nitrocellulose membrane, agarose, cross-linked dextran, and other polysaccharides.

Kits of the invention may be used to perform an enzyme-linked immunosorbent assay (ELISA). Additionally or alternatively, kits of the invention may be used to perform western blotting. Such kits may further comprise a carrier, package or container that is compartmentalized to receive one or more containers such as vials, tubes, and the like, each of the container(s) comprising one of the separate elements to be used in the method. The kits of the invention will typically comprise the container comprising the elements described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described herein. Directions and or other information can also be included on an insert which is included with the kits. The kits preferably comprises means for handling and/or processing a blood sample.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended claims, and all changes which come within the meaning and range of equivalency are intended to be embraced therein.

The foregoing description will be more fully understood with reference to the following Examples. Such Examples, are, however, exemplary of methods of practising the present invention and are not intended to limit the application and the scope of the invention.

Examples

Ethics Statement

Buffy coats of blood of healthy donors were provided by the Geneva Hospital Blood Transfusion Center. In accordance with the ethical committee of the Geneva Hospital and with the Declaration of Helsinki, the blood bank obtained informed consent from the donors, who were informed that part of their blood would be used for research purposes.

Patient Characteristics

All patients had an APS, as defined by the revised Sapporo criteria.[2] Control antibodies and peripheral blood mononuclear cells (PBMC) were isolated from blood plasma of healthy volunteers. The characteristics of the patients used in this study are listed in Table 1.

Cell Culture

Monocytes were isolated from blood buffy coats of healthy volunteers as previously described.[14, 15] Monocyte purity routinely consisted of >90% CD14$^+$ cells, <1% CD3$^+$ cells, and <1% CD19$^+$ cells as assessed by flow cytometry. Cells were cultured in RPMI containing 10% Fetal Bovine Serum (FBS; Gibco BRL-Life Technologies). Each experiment was performed with at least three different preparations of monocytes.

Recombinant β2GP1 Fusion Proteins and Peptide Libraries

Recombinant fusion proteins, corresponding to sushi domain I and II, domains III, IV and V, respectively, of β$_2$GP1 were generated. Briefly, a series of β$_2$GP1 complementary DNA (cDNA) constructs, encoding these domains, were inserted into the vector pcDNA3.1_mycHis_A_A130 between cloning sites: BamHI/XhoI. The plasmids were prepared by Life Technology (Carlsbad, CA, USA) and transfected into HEK293 cells. The fusion proteins were purified using Nickel-resin affinity chromatography (GE Healthcare) and dialysed with Amicon® Ultra (Milipore, Billerica, MA, USA). The concentration was then adjusted to 5 mg/ml in PBS. The peptides libraries were generated by Mimotopes (Clayton, Australia). Lyophilized non water-soluble peptides were reconstituted in 50% DMSO and 7.5% acetic acid before dilution in PBS. All peptides had 95% purity as assessed by Analytical RP-HPLC. Native (β2GP1 is purified from Human Plasma with 96% purity (Prospecbio, USA).

T Cell Proliferation Assays

Peripheral blood mononuclear cells (PBMC) were isolated by density gradient centrifugation over Lymphoprep™ (Axis-Shield PoC) according to the manufacturer's instructions. T cell proliferation was evaluated by 5,6-carboxylfluorescein diacetate succinimidyl ester (CFSE) dilution assays (eBioscience). PBMC were stained with 0.1 μM CFSE (eBioscience), according to the manufacturer's instructions. Cells were cultured in the presence of antigens (10 g/ml) for 10 days. T cell proliferation was assessed by flow cytometry evaluation of CFSE dilution. Proliferation was expressed as the cell division index (defined as the number of CFSE$^{low}$ T cells cultured with antigen/number of CFSE$^{low}$ T cells without antigen). In all cases, the culture medium consisted of X-VIVO 15 (Lonza, Walkersville, MD) supplemented with penicillin (100 U/ml) and streptomycin (0.1 mg/ml).

Tetramer Staining of Class II-Peptide

Staining was performed following the Benaroya research institute's protocol (https://tetramer.benaroyaresearch.org/more-inforesources/protocols). Briefly, we performed antigen specific amplification with domains I-II, i.e cells were cultured in the presence of antigens (10 μg/ml) for 10 days (pulse), prior to tetramer staining as described below. 10 μg/mL of PE-labeled Class II tetramer were added to the cells for 3 hours at 37° C. in the dark. Subsequently, cells were stained with fluorochrome (AF647)-labeled anti-CD4 for 30 minutes on ice before flow cytometry analysis.

Flow Cytometry

Single-cell suspensions stained with CFSE (eBioscience) were incubated with anti-CD32 (Biolegend) to prevent non-specific antibody binding, then stained with antibodies against AF488-CD3, AF647-CD4, (BD Bioscience) major histocompatibility complex (MHC) class II tetramer (Benaroya Research Institute). Staining was assessed with ACCURI C6 flow cytometer (BD Biosciences).

HLA Typing

Patients were matched at the second field level typing (high-resolution typing, previously referred to as 4-digit typing) for the HLA-DRB1/B3, DQB1 and DPB1 loci by standard methods: PCR-SSO on microbeads arrays (Luminex Technology, LabType HD, OneLambda, Ingen, Chilly-Mazarin, France), PCR-SSP (Genovision, Milan Analytika AG, Rheinfelden, Switzerland) and SBT (Protrans, Endotell AG, Allschwil, Switzerland).

IgG Purification

IgG fractions were isolated from patients plasma with Protein-G CL-4B Sepharose (GE Healthcare) as previously described.[16] To assay for endotoxin and lipopeptide contamination of the IgG fractions, we depleted IgG from the aPLA and IgG-ctl (control) fractions by one step of affinity adsorption to Protein G-Sepharose and tested the remaining supernatant for its capacity for monocyte activation, as previously described[17]. In addition, endotoxin levels were measured by the Limulus Amebocyte Lysate Endochrome Assay (Charles River Laboratories), and were found to be below the detection limit (0.25 EU/mL) for all IgG fractions at the concentration used in the assays. Each experiment was performed with at least 2 different preparations of IgG.

TNF Production

The cells were treated with recombinant domains or peptides of β$_2$GP1 at 10 μg/ml prior to incubation with aPLA or control IgG. Supernatants were collected for TNF quantification by ELISA (R&D System).

ELISA Epitope Mapping Assay

MaxiSorp™ 96 well plates (Nunc) were coated with 10 μg/ml recombinant domains or peptides of β$_2$GP1 prior to incubation with aPLA or control IgG. Secondary anti-human antibodies conjugated to IR800CW (Rockland) were used. Protein- or peptide-bound antibodies were detected and quantified by the Odyssey system (Li-Cor).

Western Blot

Total cell lysates were prepared and subjected to Western blot analysis as described previously.[16] The blots were probed with anti-cMyc (Zymed). Secondary antibodies conjugated to IR800CW (Rockland) were used. Antibody-bound proteins were detected and quantified by the Odyssey system (Li-Cor).

Statistical Analysis.

When required, the significance of differences between groups was assessed using the nonparametric Mann-Whitney U test. *: $p \leq 0.05$; : $p \leq 0.005$; *: $p \leq 0.0005$. All data were represented as mean±SEM of at least 3 independent experiments.

TABLE 5

| Peptides, names and SEQ ID Nos | |
|---|---|
| Peptide name | SEQ ID NO: |
| Dom I-II | 37 |
| p1 | 32 |
| p2 | 38 |
| p3 | 39 |
| p4 | 35 |
| p5 | 40 |

TABLE 5-continued

Peptides, names and SEQ ID Nos

| Peptide name | SEQ ID NO: |
|---|---|
| p6 | 33 |
| p7 | 41 |
| p8 | 42 |
| p9 | 43 |
| p10 | 44 |
| p11 | 45 |
| p12 | 46 |
| p13 | 47 |
| revp3 | 34 |
| revCD40 | 36 |

REFERENCES

1. Giannakopoulos B, Krilis S A. The pathogenesis of the antiphospholipid syndrome. *N Engl J Med.* 2013; 368:1033-1044
2. Miyakis S, Lockshin M D, Atsumi T, Branch D W, Brey R L, Cervera R, Derksen R H, P G DEG, Koike T, Meroni P L, Reber G, Shoenfeld Y, Tincani A, Vlachoyiannopoulos P G, Krilis S A. International consensus statement on an update of the classification criteria for definite antiphospholipid syndrome (aps). *J Thromb Haemost.* 2006; 4:295-306
3. Agar C, van Os G M, Morgelin M, Sprenger R R, Marquart J A, Urbanus R T, Derksen R H, Meijers J C, de Groot P G. Beta2-glycoprotein i can exist in 2 conformations: Implications for our understanding of the antiphospholipid syndrome. *Blood.* 2010; 116:1336-1343
4. de Laat B, van Berkel M, Urbanus R T, Siregar B, de Groot P G, Gebbink M F, Maas C. Immune responses against domain i of beta(2)-glycoprotein i are driven by conformational changes: Domain i of beta(2)-glycoprotein i harbors a cryptic immunogenic epitope. *Arthritis Rheum.* 2011; 63:3960-3968
5. de Laat B, Derksen R H, van Lummel M, Pennings M T, de Groot P G. Pathogenic anti-beta2-glycoprotein i antibodies recognize domain i of beta2-glycoprotein i only after a conformational change. *Blood.* 2006; 107:1916-1924
6. Iverson G M, Reddel S, Victoria E J, Cockerill K A, Wang Y X, Marti-Renom M A, Sali A, Marquis D M, Krilis S A, Linnik M D. Use of single point mutations in domain i of beta(2)-glycoprotein i to determine fine antigenic specificity of antiphospholipid autoantibodies. *J Immunol.* 2002; 169:7097-7103
7. Ioannou Y, Pericleous C, Giles I, Latchman D S, Isenberg D A, Rahman A. Binding of antiphospholipid antibodies to discontinuous epitopes on domain i of human beta(2)-glycoprotein i: Mutation studies including residues r39 to r43. *Arthritis Rheum.* 2007; 56:280-290
8. Khattri S, Zandman-Goddard G, Peeva E. B-cell directed therapies in antiphospholipid antibody syndrome—new directions based on murine and human data. *Autoimmun Rev.* 2012; 11:717-722
9. Cousins L, Pericleous C, Khamashta M, Bertolaccini M L, Ioannou Y, Giles I, Rahman A. Antibodies to domain i of beta-2-glycoprotein i and iga antiphospholipid antibodies in patients with 'seronegative' antiphospholipid syndrome. *Ann Rheum Dis.* 2015; 74:317-319
10. Hattori N, Kuwana M, Kaburaki J, Mimori T, Ikeda Y, Kawakami Y. T cells that are autoreactive to beta(2)-glycoprotein i in patients with antiphospholipid syndrome and healthy individuals. *Arthritis and Rheumatism.* 2000; 43:65-75
11. Arai T, Yoshida K, Kaburaki J, Inoko H, Ikeda Y, Kawakami Y, Kuwana M. Autoreactive cd4(+) t-cell clones to beta2-glycoprotein i in patients with antiphospholipid syndrome: Preferential recognition of the major phospholipid-binding site. *Blood.* 2001; 98:1889-1896
12. Ito H, Matsushita S, Tokano Y, Nishimura H, Tanaka Y, Fujisao S, Mitsuya H, Hashimoto H, Nishimura Y. Analysis oft cell responses to the β2-glycoprotein i-derived peptide library in patients with anti-p2-glycoprotein i antibody-associated autoimmunity. *Human Immunology.* 2000; 61:366-377
13. Brandt K J, Kruithof E K O, de Moerloose P. Receptors involved in cell activation by antiphospholipid antibodies. *Thrombosis Research.* 2013; 132:408-413
14. Brandt K J, Fickentscher C, Kruithof E K, de Moerloose P. Tlr2 ligands induce nf-kappab activation from endosomal compartments of human monocytes. *PLoS One.* 2013; 8:e80743
15. Mentzer S J, Guyre P M, Burakoff S J, Faller D V. Spontaneous aggregation as a mechanism for human monocyte purification. *Cellular Immunology.* 1986; 101:312-319
16. Brandt K J, Fickentscher C, Boehlen F, Kruithof E K, de Moerloose P. Nf-kappab is activated from endosomal compartments in antiphospholipid antibodies-treated human monocytes. *J Thromb Haemost.* 2014; 12:779-791
17. Satta N, Kruithof E K, Fickentscher C, Dunoyer-Geindre S, Boehlen F, Reber G, Burger D, de Moerloose P. Toll-like receptor 2 mediates the activation of human monocytes and endothelial cells by antiphospholipid antibodies. *Blood.* 2011; 117:5523-5531
18. de Laat B, de Groot P G. Autoantibodies directed against domain i of beta2-glycoprotein i. *Curr Rheumatol Rep.* 2011; 13:70-76
19. Vlachoyiannopoulos P G, Mavragani C P, Bourazopoulou E, Balitsari A V, Routsias J G. Anti-cd40 antibodies in antiphospholipid syndrome and systemic lupus erythematosus. *Thromb Haemost.* 2004; 92:1303-1311
20. Tanimura K, Jin H, Suenaga T, Morikami S, Arase N, Kishida K, Hirayasu K, Kohyama M, Ebina Y, Yasuda S, Horita T, Takasugi K, Ohmura K, Yamamoto K, Katayama I, Sasazuki T, Lanier L L, Atsumi T, Yamada H, Arase H. B2-glycoprotein i/hla class ii complexes are novel autoantigens in antiphospholipid syndrome. *Blood.* 2015; 125:2835-2844
21. Domenico Sebastiani G, Minisola G, Galeazzi M. Hla class ii alleles and genetic predisposition to the antiphospholipid syndrome. *Autoimmun Rev.* 2003; 2:387-394
22. Anjos S, Nguyen A, Ounissi-Benkalha H, Tessier M C, Polychronakos C. A common autoimmunity predisposing signal peptide variant of the cytotoxic t-lymphocyte antigen 4 results in inefficient glycosylation of the susceptibility allele. *J Biol Chem.* 2002; 277:46478-46486
23. Smith L R, Bost K L, Blalock J E. Generation of idiotypic and anti-idiotypic antibodies by immunization with peptides encoded by complementary ma: A possible molecular basis for the network theory. *J Immunol.* 1987; 138:7-9
24. Pendergraft W F, Preston G A, Shah R R, Tropsha A, Carter C W, Jennette J C, Falk R J. Autoimmunity is triggered by cpr-3(105-201), a protein complementary to human autoantigen proteinase-3. *Nature medicine.* 2004; 10:72-79

25. ager U, Lunder M, Hodnik V, Anderluh G, Čučnik S, Kveder T, Božič B. Significance of k(l/v)wx(i/l/v)p epitope of the b2gpi in its (patho)physiologic function. *EJIFCC*. 2011; 22:118-124
26. Blank M, Krouse I, Fridkin M, Keller N, Kopolovic J, Goldberg I. Bacterial induction of autoantibodies to b2-glycoprotein-1 accounts for the infectious etiology of antiphospholipid syndrome. *J Clin Invest*. 2002; 109:797-804
27. Toyoshima M, Maegaki Y, Yotsumata K, Takei S, Kawano Y. Antiphospholipid syndrome associated with human herpesvirus-6 infection. *Pediatr Neurol*. 2007; 37:449-451
28. Grunewald T, Burmester G R, Schuler-Maue W, Hiepe F, Buttgereit F. Antiphospholipid antibodies and cd5+ b cells in hiv infection. *Clin Exp Immunol*. 1999; 115:464-471
29. Abdel-Wahab N, Lopez-Olivo M A, Pinto-Patarroyo G P, Suarez-Almazor M E. Systematic review of case reports of antiphospholipid syndrome following infection. *Lupus*. 2016; 25:1520-1531
30. Durkin M L, Marchese D, Robinson M D, Ramgopal M. Catastrophic antiphospholipid syndrome (caps) induced by influenza a virus subtype h1n1. *BMJ Case Rep*. 2013; 2013:bcr2013200474
31. McNeil H P, Simpson R J, Chesterman C N, Krilis S A. Antiphospholipid antibodies are directed against a complex antigen includes a lipid-binding inhibitor of coagulation: B2-glycoprotein i (apolipoprotein h). *Proc. Natl. Acad. Sci. USA*. 1990; 87:4120-4124
32. Satta N, Dunoyer-Geindre S, Reber G, Fish R J, Boehlen F, Kruithof E K, de Moerloose P. The role of tlr2 in the inflammatory activation of mouse fibroblasts by human antiphospholipid antibodies. *Blood*. 2007; 109:1507-1514
33. Lutters B C, Derksen R H, Tekelenburg W L, Lenting P J, Arnout J, de Groot P G. Dimers of beta 2-glycoprotein i increase platelet deposition to collagen via interaction with phospholipids and the apolipoprotein e receptor 2'. *J Biol Chem*. 2003; 278:33831-33838
34. Döring Y, Hurst J, Lorenz M, Prinz N, Clemens N, Drechsler M D, Bauer S, Chapman J, Shoenfeld Y, Blank M. Human antiphospholipid antibodies induce tnfa in monocytes via toll-like receptor 8. *Immunobiology*. 2010; 215:230-241
35. Romay-Penabad Z, Montiel-Manzano M G, Shilagard T, Papalardo E, Vargas G, Deora A B, Wang M, Jacovina A T, Garcia-Latorre E, Reyes-Maldonado E, Hajjar K A, Pierangeli S S. Annexin a2 is involved in antiphospholipid antibody-mediated pathogenic effects in vitro and in vivo. *Blood*. 2009; 114:3074-3083
36. Pierangeli S S, Vega-Ostertag M E, Raschi E, Liu X, Romay-Penabad Z, De Micheli V, Galli M, Moia M, Tincani A, Borghi M O, Nguyen-Oghalai T, Meroni P L. Toll-like receptor and antiphospholipid mediated thrombosis: In vivo studies. *Ann Rheum Dis*. 2007; 66:1327-1333
37. Hurst J, Prinz N, Lorenz M, Bauer S, Chapman J, Lackner K J, von Landenberg P. Tlr7 and tlr8 ligands and antiphospholipid antibodies show synergistic effects on the induction of il-1β and caspase-1 in monocytes and dendritic cells. *Immunobiology*. 2009; 214:683-691
38. Aguilar-Valenzuela R, Nickerson K, Romay-Penabad Z, Shlomchik M J, Vargas G, Shilagard T, Pierangeli S S. Involvement of tlr7 and tlr9 in the production of antiphospholipid antibodies. *Arthritis and Rheumatism*. 2011; 63:S281-S282
39. Shi T, Giannakopoulos B, Yan X, Yu P, Berndt M C, Andrews R K, Rivera J, Iverson G M, Cockerill K A, Linnik M D, Krilis S A. Anti-β2-glycoprotein i antibodies in complex with β2-glycoprotein i can activate platelets in a dysregulated manner via glycoprotein ib-ix-v. *Arthritis Rheum*. 2006; 54:2558-2567

---

The invention claimed is:

1. An isolated peptide consisting of the amino acid sequence (SEQ ID NO:51)

$$X_1\text{-}X_2\text{-}X_3\text{-}X_4\text{-}X_5\text{-}F\text{-}X_7\text{-}X_8$$

wherein
- $X_1$, $X_2$, $X_3$ and $X_8$ are nonpolar amino acid residues, each independently selected from the group consisting of A, V, I, L, M, F, W, C, P and G;
- $X_4$ and $X_5$ are polar amino acid residues, each independently selected from the group consisting of Y, T, S, H, K, R, E, D, Q and N;
- $X_7$ is any amino acid residue selected from the group consisting of A, V, I, L, M, F, W, C, P, G, Y, T, S, H, K, R, E, D, Q and N;
- and a linker at N- and/or C-terminus; wherein the linker at the N- and/or C-terminus is a poly-Gly linker.

2. The isolated peptide of claim 1, wherein the linker at N- and/or C-terminus is independently selected from the group consisting of SEQ ID NO:1, SEQ ID NO:2, SEQ ID NO:3, SEQ ID NO:60, SEQ ID NO:61, SEQ ID NO:62, SEQ ID NO:63, and SEQ ID NO:64.

3. A pharmaceutical composition comprising the isolated peptide of claim 1 in an amount effective to prevent, reduce or inhibit one or more symptoms of antiphospholipid syndrome (APS) in a subject in need thereof, and a pharmaceutically acceptable carrier for administration of the isolated peptide.

4. A MHC composition comprising MHC class II molecules and the isolated peptide of claim 1.

5. The MHC composition of claim 4 further comprising an inducer of cell death.

6. The MHC composition of claim 5, wherein the inducer of cell death is associated to streptavidine and MHC class II molecules are further modified by a binding moiety.

7. The MHC composition of claim 5, wherein the inducer of cell death is selected from the group consisting of doxorubicin, epirubicin, idarubicin, mitoxantrone, bleomycin, bortezomib, cyclophosphamide, the type I ribosome-inactivating protein saporin and oxaliplatin.

8. The MHC composition of claim 4, wherein the MHC class II molecules are tetramers or dextramers.

9. The MHC composition of claim 4, wherein the composition is a soluble composition.

10. The MHC composition of claim 4, wherein the composition is attached to an insoluble carrier or a substrate.

11. A method for treating antiphospholipid syndrome (APS) in a subject in need thereof, the method comprising administering to said subject a therapeutically effective amount of the MHC composition of claim 5.

12. A method for preventing and/or inhibiting one or more symptoms of antiphospholipid syndrome (APS) in a subject in need thereof, the method comprising administering to said subject a therapeutically effect amount of the isolated peptide of claim 1 or the pharmaceutical composition thereof.

13. A method for detecting the presence of antiphospholipid antibody in a sample, the method comprising
  (i) contacting the sample with the isolated peptide of claim 1 under conditions allowing for the formation of a complex between antiphospholipid antibodies with the isolated peptide; and
  (ii) detecting the complex using an immunoassay.

14. The method of claim 13, wherein the isolated peptide of claim 1 is immobilized on a surface or on beads.

15. The method of claim 13, wherein the complex is detected using a secondary antibody against the Fc portion of the antiphospholipid.

16. The method of claim 15, wherein the antiphospholipid antibody is an IgG-antibody and the secondary antibody is an anti-IgG antibody.

17. The method of claim 15, wherein the secondary antibody is labelled with a detectable marker.

18. The method of claim 13, wherein the immunoassay is selected from the group consisting of immunoprecipitation, enzyme immunoassay (EIA), radioimmunoassay (RIA) or fluorescence immunoassay, a chemilumineszent assay, an agglutination assay, nephelometric assay, turbidimetric assay, a Western blot, a competitive immunoassay, a non-competitive immunoassay, a homogeneous immunoassay, a heterogeneous immunoassay, a bioassay and a reporter-assay.

19. A kit for detecting in a sample the presence or absence of an antiphospholipid antibody, the kit comprising one or more isolated peptide of claim 1.

* * * * *

SEQUENCE LISTING

```
<160> NUMBER OF SEQ ID NOS: 64

<210> SEQ ID NO 1
<211> LENGTH: 16
<212> TYPE: PRT
<213> ORGANISM: Artificial Sequence
<220> FEATURE:
<223> OTHER INFORMATION: Synthetic sequence

<400> SEQUENCE: 1

Gly Gly Gly Gly Ser Leu Val Pro Arg Gly Ser Gly Gly Gly Gly Ser
1               5                   10                  15

<210> SEQ ID NO 2
<211> LENGTH: 6
<212> TYPE: PRT
<213> ORGANISM: Artificial Sequence
<220> FEATURE:
<223> OTHER INFORMATION: Synthetic sequence

<400> SEQUENCE: 2

Gly Ser Gly Ser Gly Ser
1               5

<210> SEQ ID NO 3
<211> LENGTH: 11
<212> TYPE: PRT
<213> ORGANISM: Artificial Sequence
```

-continued

<220> FEATURE:
<223> OTHER INFORMATION: Synthetic sequence

<400> SEQUENCE: 3

Gly Ser Gly Gly Gly Thr Gly Gly Ser Gly
1               5                   10

<210> SEQ ID NO 4
<211> LENGTH: 20
<212> TYPE: PRT
<213> ORGANISM: Homo sapiens

<400> SEQUENCE: 4

Met Ile Ser Pro Val Leu Ile Leu Phe Ser Ser Phe Leu Cys His Val
1               5                   10                  15

Ala Ile Ala Gly
            20

<210> SEQ ID NO 5
<211> LENGTH: 8
<212> TYPE: PRT
<213> ORGANISM: Homo sapiens

<400> SEQUENCE: 5

Ala Gly Gly Asn Asn Phe Ile Cys
1               5

<210> SEQ ID NO 6
<211> LENGTH: 8
<212> TYPE: PRT
<213> ORGANISM: Homo sapiens

<400> SEQUENCE: 6

Cys Leu Ile Asp Gln Phe Arg Cys
1               5

<210> SEQ ID NO 7
<211> LENGTH: 8
<212> TYPE: PRT
<213> ORGANISM: Homo sapiens

<400> SEQUENCE: 7

Gly Val Leu Tyr Asn Phe Glu Leu
1               5

<210> SEQ ID NO 8
<211> LENGTH: 8
<212> TYPE: PRT
<213> ORGANISM: Homo sapiens

<400> SEQUENCE: 8

Val Ala Ile Gln Asp Phe Thr Cys
1               5

<210> SEQ ID NO 9
<211> LENGTH: 8
<212> TYPE: PRT
<213> ORGANISM: Homo sapiens

<400> SEQUENCE: 9

Ile Leu Phe Ser Ser Phe Leu Cys
1               5

<210> SEQ ID NO 10

```
<211> LENGTH: 8
<212> TYPE: PRT
<213> ORGANISM: Homo sapiens

<400> SEQUENCE: 10

Gly Gly Met Arg Lys Phe Ile Cys
1               5

<210> SEQ ID NO 11
<211> LENGTH: 8
<212> TYPE: PRT
<213> ORGANISM: Homo sapiens

<400> SEQUENCE: 11

Pro Val Val Thr Ser Phe Pro Leu
1               5

<210> SEQ ID NO 12
<211> LENGTH: 8
<212> TYPE: PRT
<213> ORGANISM: Homo sapiens

<400> SEQUENCE: 12

Cys Leu Phe Ser Ser Phe Leu Ile
1               5

<210> SEQ ID NO 13
<211> LENGTH: 8
<212> TYPE: PRT
<213> ORGANISM: Homo sapiens

<400> SEQUENCE: 13

Pro Pro Leu His Asp Phe Tyr Cys
1               5

<210> SEQ ID NO 14
<211> LENGTH: 8
<212> TYPE: PRT
<213> ORGANISM: Homo sapiens

<400> SEQUENCE: 14

Gly Cys Gly Glu Arg Phe Arg Cys
1               5

<210> SEQ ID NO 15
<211> LENGTH: 8
<212> TYPE: PRT
<213> ORGANISM: Homo sapiens

<400> SEQUENCE: 15

Cys Gly Ala His Glu Phe Gln Cys
1               5

<210> SEQ ID NO 16
<211> LENGTH: 8
<212> TYPE: PRT
<213> ORGANISM: Homo sapiens

<400> SEQUENCE: 16

Cys Gly Pro Thr Gln Phe Arg Cys
1               5

<210> SEQ ID NO 17
<211> LENGTH: 8
<212> TYPE: PRT
```

```
<213> ORGANISM: Homo sapiens

<400> SEQUENCE: 17

Cys Gly Gly Tyr Gln Phe Thr Cys
1               5

<210> SEQ ID NO 18
<211> LENGTH: 8
<212> TYPE: PRT
<213> ORGANISM: Homo sapiens

<400> SEQUENCE: 18

Cys Leu Ala Asp Glu Phe Lys Cys
1               5

<210> SEQ ID NO 19
<211> LENGTH: 8
<212> TYPE: PRT
<213> ORGANISM: Homo sapiens

<400> SEQUENCE: 19

Cys Pro Pro His Glu Phe Lys Cys
1               5

<210> SEQ ID NO 20
<211> LENGTH: 8
<212> TYPE: PRT
<213> ORGANISM: Homo sapiens

<400> SEQUENCE: 20

Cys Trp Leu Asp Asp Phe Asn Cys
1               5

<210> SEQ ID NO 21
<211> LENGTH: 8
<212> TYPE: PRT
<213> ORGANISM: Homo sapiens

<400> SEQUENCE: 21

Cys Ala Pro His Glu Phe Gln Cys
1               5

<210> SEQ ID NO 22
<211> LENGTH: 8
<212> TYPE: PRT
<213> ORGANISM: Homo sapiens

<400> SEQUENCE: 22

Cys Gly Pro Arg Glu Phe Arg Cys
1               5

<210> SEQ ID NO 23
<211> LENGTH: 8
<212> TYPE: PRT
<213> ORGANISM: Homo sapiens

<400> SEQUENCE: 23

Ile Ile Gly Glu Thr Phe His Cys
1               5

<210> SEQ ID NO 24
<211> LENGTH: 8
<212> TYPE: PRT
<213> ORGANISM: Homo sapiens
```

```
<400> SEQUENCE: 24

Ile Leu Gly Glu Thr Phe Arg Cys
1               5

<210> SEQ ID NO 25
<211> LENGTH: 8
<212> TYPE: PRT
<213> ORGANISM: Homo sapiens

<400> SEQUENCE: 25

Gly Pro Leu Arg Thr Phe Val Cys
1               5

<210> SEQ ID NO 26
<211> LENGTH: 8
<212> TYPE: PRT
<213> ORGANISM: Homo sapiens

<400> SEQUENCE: 26

Cys Pro Pro Thr Lys Phe Gln Cys
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic sequence

<400> SEQUENCE: 27

Ile Leu Phe Ser Ser Phe Leu Cys
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic sequence

<400> SEQUENCE: 28

Gly Gly Met Arg Lys Phe Ile Cys
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic sequence

<400> SEQUENCE: 29

Pro Val Val Thr Ser Phe Pro Leu
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic sequence

<400> SEQUENCE: 30

Ile Leu Phe Ala Ser Phe Leu Cys
1               5
```

```
<210> SEQ ID NO 31
<211> LENGTH: 8
<212> TYPE: PRT
<213> ORGANISM: Artificial Sequence
<220> FEATURE:
<223> OTHER INFORMATION: Synthetic sequence

<400> SEQUENCE: 31

Gly Gly Met Arg Ala Phe Ile Cys
1               5

<210> SEQ ID NO 32
<211> LENGTH: 20
<212> TYPE: PRT
<213> ORGANISM: Homo sapiens

<400> SEQUENCE: 32

Met Ile Ser Pro Val Leu Ile Leu Phe Ser Ser Phe Leu Cys His Val
1               5                   10                  15

Ala Ile Ala Gly
            20

<210> SEQ ID NO 33
<211> LENGTH: 20
<212> TYPE: PRT
<213> ORGANISM: Homo sapiens

<400> SEQUENCE: 33

Cys Lys Pro Gly Tyr Val Ser Arg Gly Gly Met Arg Lys Phe Ile Cys
1               5                   10                  15

Pro Leu Thr Gly
            20

<210> SEQ ID NO 34
<211> LENGTH: 16
<212> TYPE: PRT
<213> ORGANISM: Artificial Sequence
<220> FEATURE:
<223> OTHER INFORMATION: Synthetic sequence

<400> SEQUENCE: 34

Phe Thr Lys Leu Pro Val Val Thr Ser Phe Pro Leu Asp Asp Pro Lys
1               5                   10                  15

<210> SEQ ID NO 35
<211> LENGTH: 19
<212> TYPE: PRT
<213> ORGANISM: Homo sapiens

<400> SEQUENCE: 35

Phe Ser Thr Val Val Pro Leu Lys Thr Phe Tyr Glu Pro Gly Glu Glu
1               5                   10                  15

Ile Thr Tyr

<210> SEQ ID NO 36
<211> LENGTH: 11
<212> TYPE: PRT
<213> ORGANISM: Artificial Sequence
<220> FEATURE:
<223> OTHER INFORMATION: Synthetic sequence

<400> SEQUENCE: 36

Gly Pro Leu Asp Asp Pro Phe Asn Ile Glu Gln
1               5                   10
```

<210> SEQ ID NO 37
<211> LENGTH: 138
<212> TYPE: PRT
<213> ORGANISM: Homo sapiens

<400> SEQUENCE: 37

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
            20                  25                  30

Thr Val Val Pro Leu Lys Thr Phe Tyr Glu Pro Gly Glu Glu Ile Thr
        35                  40                  45

Tyr Ser Cys Lys Pro Gly Tyr Val Ser Arg Gly Gly Met Arg Lys Phe
    50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Glu Gly
        115                 120                 125

Lys Trp Ser Pro Glu Leu Pro Val Cys Ala
    130                 135

<210> SEQ ID NO 38
<211> LENGTH: 20
<212> TYPE: PRT
<213> ORGANISM: Homo sapiens

<400> SEQUENCE: 38

Ser Phe Leu Cys His Val Ala Ile Ala Gly Arg Thr Cys Pro Lys Pro
1               5                   10                  15

Asp Asp Leu Pro
            20

<210> SEQ ID NO 39
<211> LENGTH: 20
<212> TYPE: PRT
<213> ORGANISM: Homo sapiens

<400> SEQUENCE: 39

Arg Thr Cys Pro Lys Pro Asp Asp Leu Pro Phe Ser Thr Val Val Pro
1               5                   10                  15

Leu Lys Thr Phe
            20

<210> SEQ ID NO 40
<211> LENGTH: 20
<212> TYPE: PRT
<213> ORGANISM: Homo sapiens

<400> SEQUENCE: 40

Tyr Glu Pro Gly Glu Glu Ile Thr Tyr Ser Cys Lys Pro Gly Tyr Val
1               5                   10                  15

Ser Arg Gly Gly
            20

```
<210> SEQ ID NO 41
<211> LENGTH: 20
<212> TYPE: PRT
<213> ORGANISM: Homo sapiens

<400> SEQUENCE: 41

Met Arg Lys Phe Ile Cys Pro Leu Thr Gly Leu Trp Pro Ile Asn Thr
1               5                   10                  15

Leu Lys Cys Thr
            20

<210> SEQ ID NO 42
<211> LENGTH: 20
<212> TYPE: PRT
<213> ORGANISM: Homo sapiens

<400> SEQUENCE: 42

Leu Trp Pro Ile Asn Thr Leu Lys Cys Thr Pro Arg Val Cys Pro Phe
1               5                   10                  15

Ala Gly Ile Leu
            20

<210> SEQ ID NO 43
<211> LENGTH: 20
<212> TYPE: PRT
<213> ORGANISM: Homo sapiens

<400> SEQUENCE: 43

Pro Arg Val Cys Pro Phe Ala Gly Ile Leu Glu Asn Gly Ala Val Arg
1               5                   10                  15

Tyr Thr Thr Phe
            20

<210> SEQ ID NO 44
<211> LENGTH: 20
<212> TYPE: PRT
<213> ORGANISM: Homo sapiens

<400> SEQUENCE: 44

Glu Asn Gly Ala Val Arg Tyr Thr Thr Phe Glu Tyr Pro Asn Thr Ile
1               5                   10                  15

Ser Phe Ser Cys
            20

<210> SEQ ID NO 45
<211> LENGTH: 20
<212> TYPE: PRT
<213> ORGANISM: Homo sapiens

<400> SEQUENCE: 45

Glu Tyr Pro Asn Thr Ile Ser Phe Ser Cys Asn Thr Gly Phe Tyr Leu
1               5                   10                  15

Asn Gly Ala Asp
            20

<210> SEQ ID NO 46
<211> LENGTH: 20
<212> TYPE: PRT
<213> ORGANISM: Homo sapiens

<400> SEQUENCE: 46

Asn Thr Gly Phe Tyr Leu Asn Gly Ala Asp Ser Ala Lys Cys Thr Glu
1               5                   10                  15
```

```
<210> SEQ ID NO 47
<211> LENGTH: 20
<212> TYPE: PRT
<213> ORGANISM: Homo sapiens

<400> SEQUENCE: 47

Ala Asp Ser Ala Lys Cys Thr Glu Glu Gly Lys Trp Ser Pro Glu Leu
1               5                   10                  15

Pro Val Cys Ala
            20

<210> SEQ ID NO 48
<211> LENGTH: 8
<212> TYPE: PRT
<213> ORGANISM: Artificial Sequence
<220> FEATURE:
<223> OTHER INFORMATION: Synthetic sequence

<400> SEQUENCE: 48

Cys Leu Phe Ser Ser Phe Leu Ile
1               5

<210> SEQ ID NO 49
<211> LENGTH: 8
<212> TYPE: PRT
<213> ORGANISM: Homo sapiens

<400> SEQUENCE: 49

Val Pro Leu Lys Thr Phe Tyr Glu
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic sequence

<400> SEQUENCE: 50

Pro Leu Asp Asp Pro Phe Asn Ile
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(3)
<223> OTHER INFORMATION: X1, X2, X3 are nonpolar amino acid residues,
      each independently selected from the group comprising A, V, I, L,
      M, F, W, C, P and G.
<220> FEATURE:
<221> NAME/KEY: MISC_FEATURE
<222> LOCATION: (4)..(5)
<223> OTHER INFORMATION: X4, X5 are polar amino acid residues, each
      independently selected from the group comprising Y, T, S, H, K, R,
      E, D, Q and N.
<220> FEATURE:
<221> NAME/KEY: MISC_FEATURE
<222> LOCATION: (7)..(7)
<223> OTHER INFORMATION: X7 is any amino acid residue.
<220> FEATURE:
```

```
<221> NAME/KEY: MISC_FEATURE
<222> LOCATION: (8)..(8)
<223> OTHER INFORMATION: X8 is nonpolar amino acid residue selected from
      the group comprising A, V, I, L, M, F, W, C, P and G.

<400> SEQUENCE: 51

Xaa Xaa Xaa Xaa Xaa Phe Xaa Xaa
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X1 is nonpolar amino acid residue selected from
      the group comprising A, V, I, L, M, F, W, C, P and G.
<220> FEATURE:
<221> NAME/KEY: MISC_FEATURE
<222> LOCATION: (2)..(2)
<223> OTHER INFORMATION: X2 is any amino acid residue selected from the
      group comprising A, V, I, L, M, F, W, C, P, G, Y, T, S, H, K, R,
      E, D, Q and N.
<220> FEATURE:
<221> NAME/KEY: MISC_FEATURE
<222> LOCATION: (4)..(5)
<223> OTHER INFORMATION: X4, X5 are polar amino acid residue selected
      from the group comprising  Y, T, S, H, K, R, E, D, Q and N.
<220> FEATURE:
<221> NAME/KEY: MISC_FEATURE
<222> LOCATION: (6)..(8)
<223> OTHER INFORMATION: X6, X7, X8 are nonpolar amino acid residues
      selected from the group comprising A, V, I, L, M, F, W, C, P and
      G.
<220> FEATURE:
<221> NAME/KEY: MISC_FEATURE
<222> LOCATION: (6)..(8)
<223> OTHER INFORMATION: X6, X7, X8 are nonpolar amino acid residues,
      each independently selected from the group comprising A, V, I, L,
      M, F, W, C, P and G.

<400> SEQUENCE: 52

Xaa Xaa Phe Xaa Xaa Xaa Xaa Xaa
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(3)
<223> OTHER INFORMATION: X1, X2, X3 are nonpolar amino acid residues,
      each independently selected from the group comprising A, V, I, L,
      M, F, W, C, P and G.
<220> FEATURE:
<221> NAME/KEY: MISC_FEATURE
<222> LOCATION: (4)..(5)
<223> OTHER INFORMATION: X4, X5 are polar amino acid residues, each
      independently selected from the group comprising Y, T, S, H, K, R,
      E, D, Q and N.
<220> FEATURE:
<221> NAME/KEY: MISC_FEATURE
<222> LOCATION: (7)..(7)
<223> OTHER INFORMATION: X7 is any amino acid residue selected from the
      group comprising A, V, I, L, M, F, W, C, P, G, Y, T, S, H, K, R,
      E, D, Q and N.
<220> FEATURE:
<221> NAME/KEY: MISC_FEATURE
<222> LOCATION: (8)..(8)
```

```
<223> OTHER INFORMATION: X8 is nonpolar amino acid residue selected from
      the group comprising A, V, I, L, M, F, W, C, P and G.

<400> SEQUENCE: 53

Xaa Xaa Xaa Xaa Xaa Phe Xaa Cys
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(3)
<223> OTHER INFORMATION: X1, X2, X3 are nonpolar amino acid residues,
      each independently selected from the group comprising A, V, I, L,
      M, F, W, C, P and G.
<220> FEATURE:
<221> NAME/KEY: MISC_FEATURE
<222> LOCATION: (4)..(4)
<223> OTHER INFORMATION: X4 is polar amino acid residue selected from
      the group comprising Y, T, S, H, K, R, E, D, Q and N..
<220> FEATURE:
<221> NAME/KEY: MISC_FEATURE
<222> LOCATION: (6)..(6)
<223> OTHER INFORMATION: X6 is any amino acid residue selected from the
      group comprising A, V, I, L, M, F, W, C, P, G, Y, T, S, H, K, R,
      E, D, Q and N..
<220> FEATURE:
<221> NAME/KEY: MISC_FEATURE
<222> LOCATION: (7)..(7)
<223> OTHER INFORMATION: X7 is nonpolar amino acid residue selected from
      the group comprising A, V, I, L, M, F, W, C, P and G.

<400> SEQUENCE: 54

Xaa Xaa Xaa Xaa Phe Xaa Xaa
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(3)
<223> OTHER INFORMATION: X1, X2, X3 are nonpolar amino acid residues,
      each independently selected from the group comprising A, V, I, L,
      M, F, W, C, P and G.
<220> FEATURE:
<221> NAME/KEY: MISC_FEATURE
<222> LOCATION: (4)..(5)
<223> OTHER INFORMATION: X4, X5 are polar amino acid residues, each
      independently selected from the group comprising Y, T, S, H, K, R,
      E, D, Q and N.
<220> FEATURE:
<221> NAME/KEY: MISC_FEATURE
<222> LOCATION: (6)..(6)
<223> OTHER INFORMATION: X6 is nonpolar amino acid residue selected from
      the group comprising A, V, I, L, M, F, W, C, P and G.
<220> FEATURE:
<221> NAME/KEY: MISC_FEATURE
<222> LOCATION: (8)..(8)
<223> OTHER INFORMATION: X8 is any amino acid residue selected from the
      group comprising A, V, I, L, M, F, W, C, P , G, Y, T, S, H, K, R,
      E, D, Q and N.
<220> FEATURE:
<221> NAME/KEY: MISC_FEATURE
<222> LOCATION: (9)..(9)
<223> OTHER INFORMATION: X9 is nonpolar amino acid residue selected from
      the group comprising A, V, I, L, M, F, W, C, P and G.
```

-continued

```
<400> SEQUENCE: 55

Xaa Xaa Xaa Xaa Xaa Xaa Phe Xaa Xaa
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X1 is nonpolar amino acide residue selected
      from the group comprising A, V, I, L, M, F, W, C, P and G.
<220> FEATURE:
<221> NAME/KEY: MISC_FEATURE
<222> LOCATION: (2)..(2)
<223> OTHER INFORMATION: X2 is any amino acide residue selected from the
      group comprising A, V, I, L, M, F, W, C, P, G, Y, T, S, H, K, R,
      E, D, Q and N.
<220> FEATURE:
<221> NAME/KEY: MISC_FEATURE
<222> LOCATION: (4)..(4)
<223> OTHER INFORMATION: X4 is nonpolar amino acide residue selected
      from the group comprising A, V, I, L, M, F, W, C, P and G.
<220> FEATURE:
<221> NAME/KEY: MISC_FEATURE
<222> LOCATION: (5)..(6)
<223> OTHER INFORMATION: X5, X6 are polar amino acid residues, each
      independently selected from the group comprising Y, T, S, H, K, R,
      E, D, Q and N.
<220> FEATURE:
<221> NAME/KEY: MISC_FEATURE
<222> LOCATION: (7)..(9)
<223> OTHER INFORMATION: X7, X8, X9 are nonpolar amino acid residues,
      each independently selected from the group comprising A, V, I, L,
      M, F, W, C, P and G.

<400> SEQUENCE: 56

Xaa Xaa Phe Xaa Xaa Xaa Xaa Xaa Xaa
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(3)
<223> OTHER INFORMATION: X1, X2, X3 are nonpolar amino acid residues,
      each independently selected from A, V, I, L, M, F, W, C, P and G.
<220> FEATURE:
<221> NAME/KEY: MISC_FEATURE
<222> LOCATION: (4)..(5)
<223> OTHER INFORMATION: X4, X5 are polar amino acid residues, each
      independently selected from the group comprising Y, T, S, H, K, R,
      E, D, Q and N.

<400> SEQUENCE: 57

Xaa Xaa Xaa Xaa Xaa
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
```

```
<222> LOCATION: (1)..(1)
<223> OTHER INFORMATION: X1 is nonpolar amino acid residue selected from
      the group comprising A, V, I, L, M, F, W, C, P and G.
<220> FEATURE:
<221> NAME/KEY: MISC_FEATURE
<222> LOCATION: (2)..(2)
<223> OTHER INFORMATION: X2 is any amino acid residue selected from the
      group comprising A, V, I, L, M, F, W, C, P , G, Y, T, S, H, K, R,
      E, D, Q and N.
<220> FEATURE:
<221> NAME/KEY: MISC_FEATURE
<222> LOCATION: (4)..(4)
<223> OTHER INFORMATION: X4 is polar amino acid residue selected from
      the group comprising Y, T, S, H, K, R, E, D, Q and N.
<220> FEATURE:
<221> NAME/KEY: MISC_FEATURE
<222> LOCATION: (5)..(7)
<223> OTHER INFORMATION: X5, X6, X7 are nonpolar amino acid residues,
      each independently selected from the group comprising A, V, I, L,
      M, F, W, C, P and G.

<400> SEQUENCE: 58

Xaa Xaa Phe Xaa Xaa Xaa Xaa
1               5

<210> SEQ ID NO 59
<211> LENGTH: 4
<212> TYPE: PRT
<213> ORGANISM: Artificial Sequence
<220> FEATURE:
<223> OTHER INFORMATION: Synthetic sequence

<400> SEQUENCE: 59

Pro Leu Thr Gly
1

<210> SEQ ID NO 60
<211> LENGTH: 10
<212> TYPE: PRT
<213> ORGANISM: Artificial Sequence
<220> FEATURE:
<223> OTHER INFORMATION: Synthetic sequence

<400> SEQUENCE: 60

Gly Gly Gly Gly Ser Gly Gly Gly Gly Ser
1               5                   10

<210> SEQ ID NO 61
<211> LENGTH: 5
<212> TYPE: PRT
<213> ORGANISM: Artificial Sequence
<220> FEATURE:
<223> OTHER INFORMATION: Synthetic sequence

<400> SEQUENCE: 61

Gly Gly Gly Gly Ser
1               5

<210> SEQ ID NO 62
<211> LENGTH: 13
<212> TYPE: PRT
<213> ORGANISM: Artificial Sequence
<220> FEATURE:
<223> OTHER INFORMATION: Synthetic sequence

<400> SEQUENCE: 62

Gly Gly Gly Gly Ser Gly Gly Gly Gly Ser Val Ser Arg
1               5                   10
```

```
<210> SEQ ID NO 63
<211> LENGTH: 8
<212> TYPE: PRT
<213> ORGANISM: Artificial Sequence
<220> FEATURE:
<223> OTHER INFORMATION: Synthetic sequence

<400> SEQUENCE: 63

Gly Gly Gly Gly Ser Val Ser Arg
1               5

<210> SEQ ID NO 64
<211> LENGTH: 14
<212> TYPE: PRT
<213> ORGANISM: Artificial Sequence
<220> FEATURE:
<223> OTHER INFORMATION: Synthetic sequence

<400> SEQUENCE: 64

Pro Leu Thr Gly Gly Gly Gly Ser Gly Gly Gly Gly Ser
1               5                   10
```